(12) United States Patent
Cornaglia et al.

(10) Patent No.: US 12,325,022 B2
(45) Date of Patent: Jun. 10, 2025

(54) MICROFLUIDIC DEVICE, SYSTEM, AND METHOD FOR THE STUDY OF ORGANISMS

(71) Applicant: ECOLE POLYTECHNIQUE FEDERALE DE LAUSANNE (EPFL), Lausanne (CH)

(72) Inventors: Matteo Cornaglia, Bussigny-près-Lausanne (CH); Martin Gijs, Ecublens (CH); Daniel Migliozzi, Vittuone (IT)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 18/099,786

(22) Filed: Jan. 20, 2023

(65) Prior Publication Data
US 2023/0149927 A1    May 18, 2023

Related U.S. Application Data

(62) Division of application No. 15/520,085, filed as application No. PCT/IB2015/058034 on Oct. 19, 2015, now Pat. No. 11,596,945.

(30) Foreign Application Priority Data
Oct. 20, 2014  (WO) .................. PCT/IB2014/065472

(51) Int. Cl.
  *B01L 3/00* (2006.01)
  *C12Q 1/04* (2006.01)
  *G01N 33/50* (2006.01)

(52) U.S. Cl.
  CPC ... *B01L 3/502753* (2013.01); *B01L 3/502761* (2013.01); *B01L 3/5085* (2013.01); *B01L 3/5088* (2013.01); *C12Q 1/04* (2013.01); *G01N 33/5008* (2013.01); *G01N 33/5085* (2013.01); *B01L 3/502715* (2013.01); *B01L 2200/0663* (2013.01); *B01L 2400/0655* (2013.01)

(58) Field of Classification Search
None
See application file for complete search history.

(56) References Cited

PUBLICATIONS

Jung, Jaehoon, et al. "Microfluidic device for coincident multi-exposure test on C. elegans." MHS2013. IEEE, 2013. (Year: 2013).*

* cited by examiner

*Primary Examiner* — Robert J Yamasaki
(74) *Attorney, Agent, or Firm* — Nixon & Vanderhye PC

(57) ABSTRACT

The invention discloses a microfluidic device for the culture, selection and/or analysis of sample organisms such as nematodes, as well as for other biological entities such as for instance animal embryos. The device features reservoirs, culture chambers and smart filtering systems allowing for the selection of specific populations/specimens of sample organisms, thus permitting long-term cultures thereof as well as phenotypic/behavioural analyses. Systems and methods for using the microfluidic device are within the present disclosure as well.

6 Claims, 16 Drawing Sheets

(iii)

(iv)

a  Synchronization of worm population b  On-chip worm culture / treatment

MICROFLUIDIC DEVICE, SYSTEM, AND METHOD FOR THE STUDY OF ORGANISMS

CROSS-REFERENCE TO RELATED APPLICATIONS

This application is a divisional of U.S. patent application Ser. No. 15/520,085 filed Apr. 19, 2017, which is the U.S. national phase of International Application No. PCT/IB2015/058034 filed Oct. 19, 2015, which claims priority to PCT/IB2014/065472 filed Oct. 20, 2014, the entire contents of each of which are hereby incorporated by reference.

TECHNICAL FIELD

The present invention relies in the field of microfluidic systems. In particular, the present invention discloses a microfluidic device for size-based selection of sample objects such as small organisms, as well as systems and methods for culturing and studying phenotypic/behavioural characteristics of the said organisms and/or for drug screening.

BACKGROUND ART

Improving human health and evaluating the health status is nowadays a completely multi-disciplinary topic, involving many disciplines and research fields, from medicine and biology, to physics, chemistry and engineering. At the core of the main issues concerning human health, still resides the lack of a global understanding of the physiology of whole organisms, due to an extreme complexity that is very hard to grasp without multiple-parameter and integrated analytical techniques. Many efforts are constantly being done to progressively dig deeper into the secrets of the human biology to better treat diseases. Obviously, there is no possibility to directly conduct this research on humans as a whole. Hence, researchers mainly base their work on studies performed on cells and tissues, which are however not able to preserve the full information about the entire organism they originate from. When this information is absolutely necessary, thus, scientists need to address analyses on entire organisms such as mice, rats, pigs, monkeys, etc, which represent the so-called "model organisms" for investigating the different aspects of human health. Nevertheless, this approach fairly originates inevitable ethical concerns and, from a practical viewpoint, raises several other issues in terms of time and cost of the analyses. These studies, in fact, cannot involve a high number of specimens and they are therefore usually not suitable for high-throughput analyses, which are however more and more crucial for the healthcare domain.

For all these reasons, in recent years, the so-called "small model organisms" are gaining particular attention in the field, since they allow circumventing most of these issues. Analyses on small animals such as *Caenorhabditis elegans, Drosophila melanogaster, Danio rerio*, or *Xenopus laevis* keep in fact holding a high amount of biological information about the organization of a full organism, while avoiding time, cost and ethical concerns. The small size of these animals, however, highly complicates these analyses, especially when only the traditional manual pick-and-place and other manipulation techniques are available, which lack the reproducibility and throughput standards required for commercialization purposes. Microfabricated solutions, though, can definitely solve this last issue, since they allow directly operating on the same length-scale of the organisms under test, paving the way towards absolute control over the protocols and the high throughput-type analyses required by this field.

The first microfluidic "worm-chips" used for in vivo *C. elegans* manipulation and imaging first appeared in 2007. Chronis et al. (Nat. Methods 4, 727-731, doi:10.1038/nmeth1075, 2007) introduced the so-called "olfactory" and "behavior" devices, able to trap single worms and monitor their neuronal and behavioral activity. These device were fabricated in polydimethylsiloxane (PDMS) and their main constitutive part was represented by "worm-traps", optimized in size for hosting young adult worms (approximately 1 mm long and 70 µm in diameter), and characterized by a tapered end to block the worm, while still permitting analysis of its locomotion patterns in the wider section of the microfluidic channel. The group of Yanik (Proc. Nat. Acad. Sci. U.S.A. 104, 13891-13895, 2007) introduced then "high-speed microfluidic sorters", to immobilize single *C. elegans* for screening phenotypic features at sub-cellular resolution in physiologically active animals. These microfluidic devices were based on separated flow and control layers, made from flexible polymers. Microchannels were used as a flow layer, to deliver reagents and manipulate worms, while the control layer consisted of a second set of microchannels built above the flow layer. When pressurized, the channels of the control layer provided a valving function by deflection of a membrane into the flow channel, used for blocking or redirecting the flow. A "worm-clamp" microfluidic device has been instead developed by Whitesides' group (Lab Chip 7, 1515-1523, doi:10.1039/b707861g, 2007), with the goal of arraying and immobilizing *C. elegans*. This system consisted of a PDMS-based array of gradually tapered microfluidic channels, with width ranging from 100 µm down to 10 µm, over 5 mm length. All these microchannels were merging into a common inlet on one side and a common outlet on the other side. As the animals were introduced into the microchannel network, they were pushed at the end of the tapered channels, where they got stuck. Almost all the trapped worms could moreover be eventually removed from the clamps by reversing the flow direction inside the device. In another study (Lab Chip 10, 589-597, doi:10.1039/b919265d, 2010), then, the same group added circular confinement chambers to each branch of the microfluidic array described above. In this chip, worms could be cultured in the different chambers and immobilized for imaging at the adult stage by suction in the worm-clamps. Each line of the array could be selectively addressed using prefabricated screw valves. To prove the suitability of this device for performing longitudinal studies/measurements, individual worms were loaded via suction at the fourth larval stage into each confinement chamber and investigated over their lifespan. Applicability of droplet-based microfluidic devices for creating and screening an array of droplets containing *C. elegans* was also demonstrated. Clausell-Tormos et al. (Chem. Biol. 15, 875-875, doi:10.1016/j.chembiol.2008.08.004, 2008) managed to encapsulate *C. elegans* eggs, along with *E. coli* bacteria as animal feed, inside 660 nL aqueous plugs. This system has been then employed to monitor the larvae after egg hatching, during the various phases of their development. While, on the one hand, this droplet-based system is relatively simple to design and do not require complex microfluidic architecture, on the other hand, it lacks of flexibility, since it cannot isolate mother animals from their own progeny. In another work, Shi et al. (Lab Chip 8, 1432-1435, doi:10.1039/b808753a, 2008) designed a microfluidic device for worm encapsulation in isolated droplets and subsequent droplet immobilization in a trap array. This microfluidic device consisted of a T-junction droplet generator combined with a serpentine microchannel, short-circuited at each branch by a cavity for droplet trapping. The different fluidic resistances of the main flow path and the cavity-based short-circuited flow path ensured efficient droplet trapping, while around 60% of the trapped droplets contained a single worm. Lu's group (Lab Chip 10, 1862-1868, 2010) presented a method for reversible immobilization and time-lapse imaging from the L1 stage to adulthood—of worms that were cultured inside a microfluidic chip. Their PDMS microfluidic device consisted of separate flow and control layers. The flow network featured culture chambers, isolated by inlet and outlet valves, for selectively retaining and culturing the worms inside the chip. Control layer of the device comprised instead the pneumatic circuitry for valve control and a second series of channels for flowing a pre-heated solution on top of the flow layer, to precisely control its temperature. Pluronic F127 block copolymer was injected into the culture chambers for selective immobilization of the worms by temperature-dependent gelation of the Pluronic solution.

Many other microfluidic devices have been described in the related art, such as those of Casadevall i Solvas et al., (*Chem. Commun.*, 2011, 47, 9801-9803), Carr et al. (Lab Chip. 2011 Jul. 21; 11(14): 2385-2396), Ghorashian et al. (PLoS One. 2013 Sep. 17; 8(9):e74480), CN102669058, CN102972351, CN103461279, IN201100640, U.S. Pat. No. 8,702,939, US20130118411, WO 2009039284, US20100263599 and WO 2009021232.

Despite all the aforementioned achievements in the field, there is still lack of a simple, robust and standardized method for fast and high-throughput studies on *C. elegans* nematodes. Most of the existing microfluidic devices, in fact, rely on complicated designs (e.g. pressurized control layers) and on cumbersome microfluidic protocols, which prevented them from achieving the reliability and throughput standards required for commercialization.

SUMMARY OF INVENTION

The present invention discloses a microfluidic device, as well as systems and methods using the same, useful for the study of phenotypic or behavioural characteristics of sample organisms, and for other applications such as for instance screening of chemical/biological compounds having a biological activity. The microfluidic device comprises culture chambers, reservoirs and filtering structures acting as passive valves for a controlled passage of the selected organisms. Said valve filters connect the reservoirs with the culture chambers, and these latter among them. By applying a pressure to a reservoir, the sample organisms are allowed to pass through the valves from said reservoir to the culture chambers, thus permitting the subsequent culture thereof. The filtering mechanism can be based on both the size and/or material of the valve filters and the size of the sample organism, as well as on the applied pressure.

In one aspect the invention relates to a microfluidic device for the study of phenotypic or behavioural characteristics of sample organisms, and for other applications such as for instance screening of chemical/biological compounds having a biological activity, said device comprising:

at least one inlet reservoir adapted to contain at least one organism;
at least one culture chamber in fluidic connection with said inlet reservoir; and
a valve filter located between said inlet reservoir and said culture chamber wherein said inlet reservoir is operatively connectable to pressure means adapted to generate a pressure within said inlet reservoir, in a way as to push its content, or at least a part of it, into said culture chamber.

In one embodiment, the valve filters of the microfluidic device are soft passive valve filters.

In one embodiment, the sample organisms are translucent organisms.

In a preferred embodiment, the microfluidic device further comprises an outlet reservoir in fluidic connection with said culture chamber and comprising another valve filter located between said culture chamber and said outlet reservoir.

In one embodiment, the outlet reservoir is operatively connectable to pressure means adapted to generate a pressure within it in a way as to draw its content or at least a part of it.

In a particular embodiment, the microfluidic device comprises one or more adjacent culture chambers or channels of consecutive culture chambers, wherein the chamber in direct connection with the inlet reservoir is the proximal chamber and the chamber in direct connection with the outlet reservoir is the distal chamber.

In a further aspect, the invention relates to a system comprising:
a microfluidic device as defined above; and
pressure means operatively connected to at least one reservoir.

In a further aspect, the invention relates to a system for culturing and analysing a population of sample organisms comprising:
a system as defined above; and
detection means arranged to detect specific parameters or phenotypic and/or behavioural characteristics of said population of sample organisms cultured in the culture chambers.

In a still further aspect, the invention relates to a method for culturing a population of sample organisms by using a system as defined above comprising the step of:
providing a population of sample organisms in a fluid culture medium for culture thereof within the inlet reservoir;
applying a pulse pressure to a reservoir so that the fluid culture medium and at least one organism can pass from the inlet reservoir to the at least one culture chamber through the valve filters; and
culturing the sample organisms by applying a pressure to a reservoir such that only the fluid culture medium can pass through the valve filters from the inlet reservoir to all the device elements in fluidic connection among them.

In a still further aspect, the invention relates to a method for culturing and analysing a population of sample organisms by using a system as defined above comprising the step of:
providing a population of sample organisms and a fluid culture medium for culture thereof within at least one inlet reservoir;
applying a pulse pressure to at least one inlet reservoir so that the fluid culture medium and at least one organism can pass from at least one inlet reservoir to the at least one culture chamber through the valve filters;
culturing the sample organisms by applying a pressure to at least one inlet reservoir such that only the fluid culture medium can pass through the valve filters from at least one inlet reservoir to all the device elements in fluidic connection among them; and analysing the sample organisms by detecting specific parameters or phenotypic and/or behavioural characteristics thereof.

In one embodiment, the pulse pressure of the above methods is such that only sample organisms of a specific size can pass through the valve filters.

The invention further relates to a method for screening active compounds by using a system as defined above comprising:
- providing a population of sample organisms and a fluid culture medium for culture thereof within a reservoir;
- applying a pulse pressure to said reservoir so that the fluid culture medium and at least one organism can pass from said reservoir to the at least one culture chamber through the valve filters;
- providing an active compound to be screened in the inlet reservoir;
- applying a suction from the outlet reservoir; and
- monitoring the effect of the active compound on the sample organism within the culture chamber wherein the suction is such that the organism cannot pass through the valve filters.

In one embodiment of the screening method, the inlet reservoir comprises a culture medium suitable for the culture of the sample organism.

In one embodiment of the screening method, the pulse pressure is such that only organisms of a specific size can pass through the valve filters.

In a particular embodiment of the screening method, the system used comprises at least 2 adjacent culture chambers each connected with an inlet reservoir.

In a particular embodiment of the screening method, the system used comprises one or more adjacent channels of consecutive culture chambers, each channel being connected with an inlet reservoir via the proximal chamber.

DETAILED DESCRIPTION OF THE INVENTION

Figure 1:
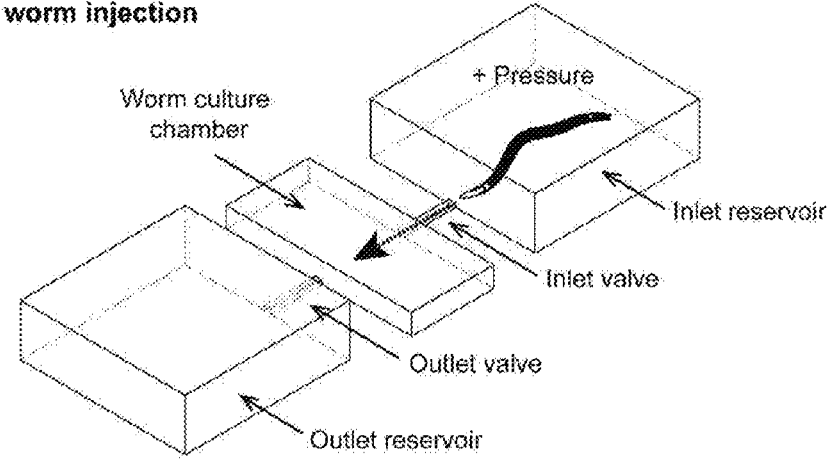
FIG. 1 depicts a schematic diagram of one embodiment of the microfluidic device.
Figure 1:
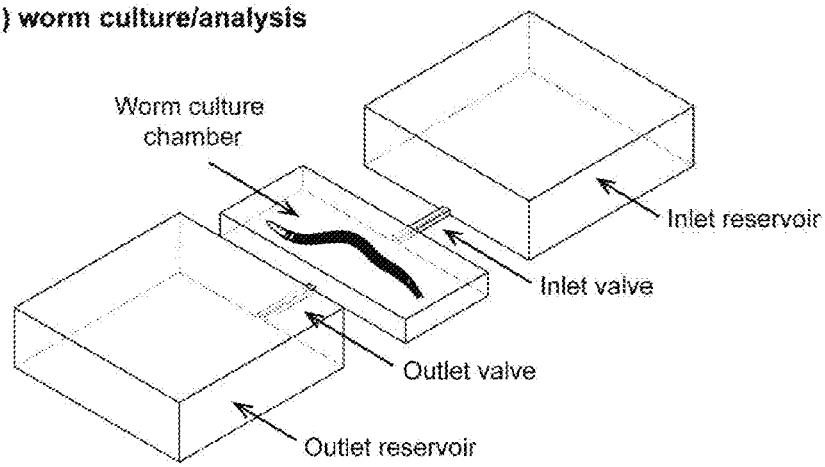
Figure 1:
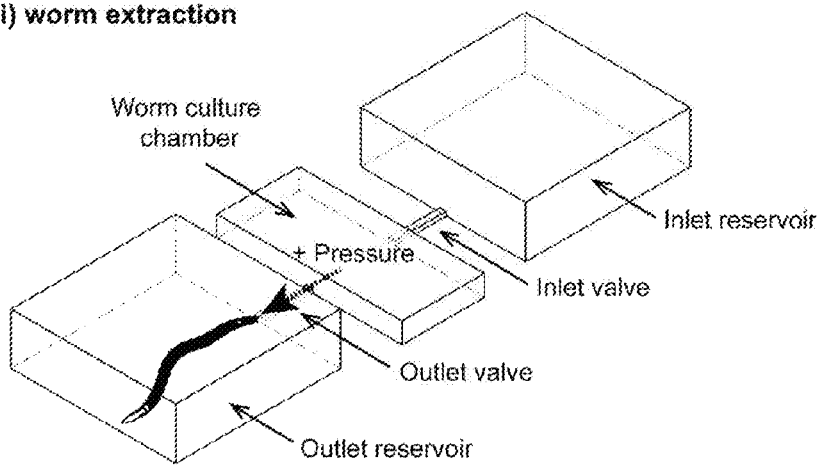

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a chamber" includes a plurality of such chambers and reference to "an organism" includes reference to one or more organisms, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

In the frame of the present disclosure, a "microfluidic device", "microfluidic chip" or "microfluidic platform" is any apparatus which is conceived to work with fluids at a micro/nanometer scale. Microfluidics is the science that deals with the flow of liquid inside channels of micrometer size. At least one dimension of the channel is of the order of a micrometer or tens of micrometers in order to consider it microfluidics. Microfluidics can be considered both as a science (study of the behaviour of fluids in micro-channels) and a technology (manufacturing of microfluidics devices for applications such as lab-on-a-chip). These technologies are based on the manipulation of liquid flow through microfabricated channels. Actuation of liquid flow is implemented either by external pressure sources, external mechanical pumps, integrated mechanical micropumps, or by combinations of capillary forces and electrokinetic mechanisms.

The microfluidic technology has found many applications such as in medicine with the laboratories on a chip because they allow the integration of many medical tests on a single chip, in cell biology research because the micro-channels have the same characteristic size as the cells and allow such manipulation of single cells and rapid change of drugs, in protein crystallization because microfluidic devices allow the generation on a single chip of a large number of crystallization conditions (temperature, pH, humidity . . . ) and also many other areas such as drug screening, sugar testers, chemical microreactor or micro fuel cells.

Generally speaking, a microfluidic chip is a set of microchannels etched or molded into a material (glass, silicon or polymers such as PDMS). The micro-channels forming the microfluidic chip are connected together in order to achieve a desired function (mix, pump, redirect and/or allow chemical reactions in a cell). This network of micro-channels trapped in the microfluidic chip is connected to the outside by inputs and outputs pierced through the chip, as an interface between the macro- and micro-world. It is through these holes that fluids (either liquids, gases or combinations thereof) are injected and removed from the microfluidic chip (through tubing, syringe adapters or even free holes in the chip). A so called "lab-on-a-chip" (LOC) is a device that integrates one or several laboratory functions on a single chip of only millimeters to a few square centimeters in size. LOCs deal with the handling of extremely small fluid volumes down to less than picoliters.

The simplest microfluidic devices consist in micro-channels molded in a polymer that is bonded to a flat surface (a glass slide as an example). The polymer most commonly used for molding microfluidic chips is polydimethylsiloxane (PDMS). The PDMS is a transparent, biocompatible (very similar to silicone gel used in breast implants), deformable, inexpensive elastomer, easy to mold and bond with glass.

In its simplest embodiment, the microfluidic device of the invention comprises two elements, i.e. an inlet reservoir and one culture chamber for the culture of sample organisms, the reservoir being operatively connectable to means for applying a pressure within it. In a preferred embodiment, the device further comprises an outlet reservoir in fluidic connection with the culture chamber. All reservoirs and chambers are delimited or separated from the consecutive elements of the device by valve filters, which function as a filtering or blocking element for the sample organisms to pass from one device element to another, while permitting fluid flow (of e.g. air, gases or liquids). However, different arrangements can be imagined, such as for instance the possibility to insert additional elements between the reservoirs and the chambers. In a very specific embodiment of the microfluidic device of the invention, for example, a serpentine element for entrapping and analyzing sample objects such as small organisms or embryos is put between a culture chamber and an outlet reservoir. All these elements are, in any case, operatively connected among them via a fluidic line.

As used herein, the wording "operatively connected", "operatively connectable" or even "operatively connecting", reflects a functional relationship between two or more components of a device or a system, that is, such a wording means that the claimed components must be connected in a way to perform a designated function. The "designated function" can change depending on the different components involved in the connection; for instance, the designated function of pressure means operatively connected to a reservoir is the ability to apply a positive or negative pressure within said reservoir in a way as to push its content, or at least a part of it. A person skilled in the art would easily understand and figure out what are the designated functions of each and every component of the device or the system of the invention, as well as their correlations, on the basis of the present disclosure.

Reservoirs and culture chambers composing the device can be made of any suitable material, preferably a transparent or translucent material allowing a direct visual monitoring of the sample organisms to be cultured. A microfluidic device having transparent reservoirs and/or culture chambers is particularly useful when it is intended to be coupled with a further imaging system for additional analyses. Any suitable reservoir can be used in the frame of the invention, such as bottles, beckers or preferably (micro)well plates such as for instance (micro)petri dishes or 96-/384-wells plates. Many inlet and/or outlet reservoirs can be present in the device of the invention, depending on experimental needs and designs. For instance, several inlet reservoirs can be included in the device of the invention, each containing different compounds and/or organisms (media, chemical compounds etc), as well as several outlet reservoirs can be placed in fluidic connection with the culture chamber(s) and used as e.g. a waste for the culture medium.

The organisms to be studied can be unicellular or multicellular organisms, or even cells. In a preferred embodiment, the sample organisms are translucent organisms. In the frame of the present disclosure, for "translucent organism" is meant any biological entity, typically in the order of few micrometers to few centimeters in size, having physical characteristics such that light can at least partially pass through it. These includes, but is not limited to, cells like somatic cells, bacteria, protozoa, protists, monerae, archaea, algae, sperms, oocytes, as well as yeasts, animal embryos or larvae and so forth. Other kind of sample organisms can be envisaged such as worms, preferably nematodes such as *C. elegans*, or *Danio rerio* and *Xenopus laevis* larvae. These organisms are cultured in a culture medium, usually a liquid or gel designed to support the growth and survival of the desired sample organisms. In the case of nematodes such as *C. elegans*, the culture medium can comprise bacteria such as *E. coli*. The chamber, or an array of chambers, is designed to run long-term cultures of such sample organisms thanks to the characteristic features of the device and the valve filters in particular.

The inlet reservoir is directly or indirectly (by e.g. tubular elements or microchannels) operatively connected with the culture chamber, or with a so-called "proximal" chamber when more than one chamber is present in the device, through an inlet valve filter. In the same way, the culture chamber is operatively connected with the outlet reservoir, or with a so-called "distal" chamber when more than one chamber is present in the device, through an outlet valve filter. The valve filters also connect the chambers among them when the device comprises more than one chamber. In this alternative, the chambers are arranged into a channel of consecutive chambers, but even an array of adjacent chambers or of adjacent channels of consecutive chambers can be envisaged.

The valves act as passive filters and can be made of any suitable material and shape, as will be detailed later in this disclosure. With the term "passive" is meant that the valves are not connected with an actuator such as a micropump expressly inserted in the chip to directly alter the valve's shape. The term "filter" denotes a structural property of the valve, i.e. its three-dimensional geometry that acts as a size-dependent barrier for solid objects suspended in a fluid medium.

For their nature and structure, the valve filters act as normally closed barriers that, in some embodiments, can be timely opened by a pressure increase within a reservoir or a chamber. However, contrary to the most common used valves exploited in microfluidic devices, the valve filters of the invention do not comprise structures such as flexible diaphragms of e.g. polymeric materials directly activated through piezoelectrical, electrostatic or (thermo)pneumatical actuators. This has the advantages of e.g. simplifying the design of the microfluidic chip and avoiding external control (thus greatly diminishing the power requirements). An overview of microvalves utilised in microfluidic devices can be found in "A review of microvalves", J. Micromech. Microeng. 16 (2006) R13-R39.

Figure 2:
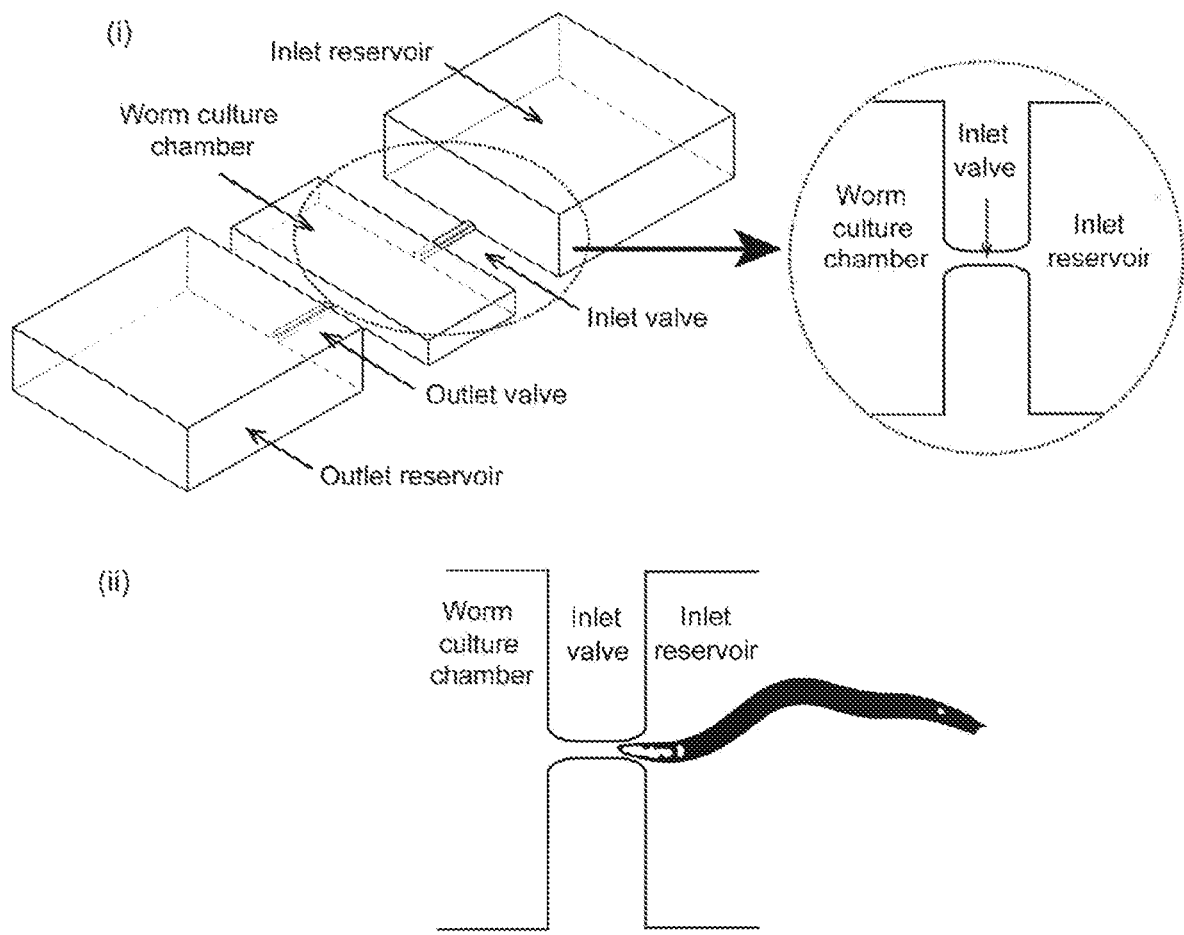
FIG. 2 depicts a schematic three-dimensional (3D) view and top-view of the portion of the microfluidic device at the valve filter (i) and a schematic description of the worm-valve mechanism (ii-iv).
Figure 2:
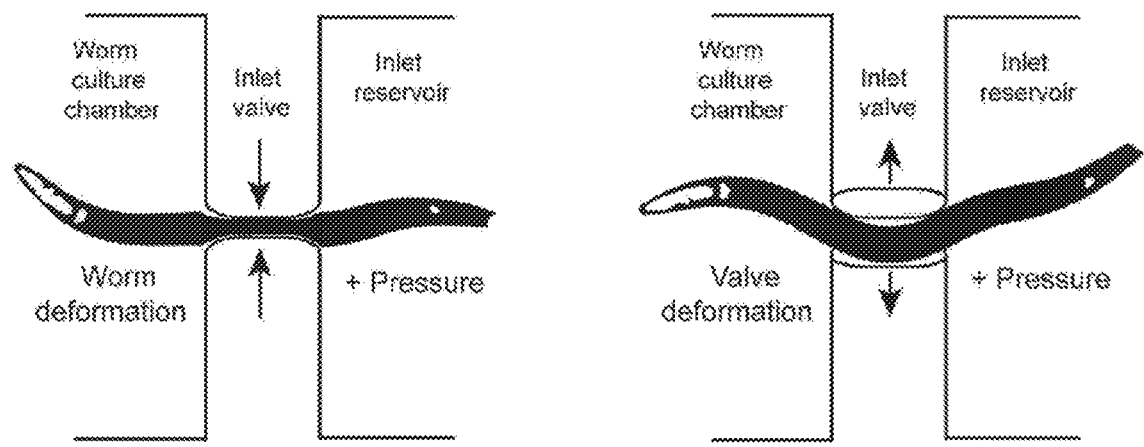
Figure 2:
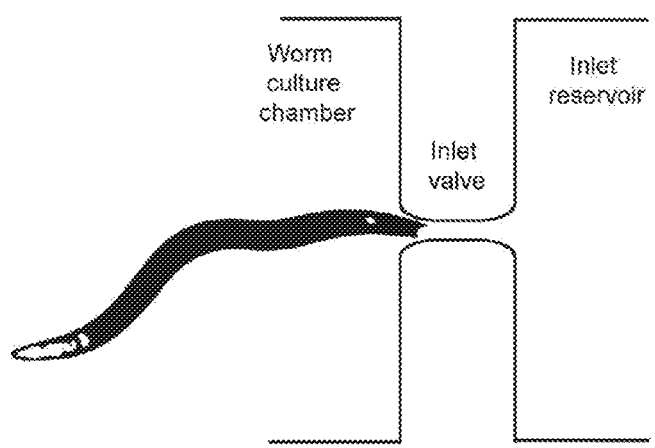

The filtering action is exerted through the particular design of the valve filter, which is finely tailored in order to exploit the nature of the sample organisms, the nature of the filter or both (see for instance FIG. 2).

In general terms, the valve filters can be made of any suitable shape and material, as long as they act as a passive filtering valve for the sample organisms of choice. In some aspects of the invention, a filtering valve is substantially made of a polymeric material. A polymeric material can be in some aspects advantageous over other materials in terms of, inter alia, biocompatibility, possibility of easy sterilization and handling concerning the manufacture, and could also permit to manufacture the entire device of the invention with rapid and cheap process by producing a monolithic body article, thus bypassing any assembling issue. For instance, a prefabricated mold can be designed and built-up in order to obtain a device with desired peculiarities (e.g. the size and shape of the valve filters, the size and shape of the reservoirs and the like), and the entire chip can be later on molded as a unitary, integral body using well-known injection molding methods. However, as will be apparent for person skilled in the art, any suitable technique for producing a single body device can be exploited, such as for instance 3D printing, photolithography and the like.

A non-exhaustive, non-limiting list of polymeric materials suitable for the manufacture of the valve filters comprises polyacrylates, polystyrene, polypropylene, polycarbonates, polysulfones, polyesters, cyclic olefins and the like.

In some embodiment of the invention, the valve is substantially made of a soft material, such as a soft polymeric material. A "soft material" is any material that is either flexible, stretchable, reversibly compressible, malleable, ductile, elastic and/or plastic. A non-exhaustive and non-limiting list of suitable soft materials according to the present invention comprises polymeric materials such as silicone (for example polydimethylsiloxane—PDMS—), nitrile rubber, polyimide, latex, polyurethane, polyisoprene (synthetic rubber), any kind of elastomers, the Tango family of rubber-like materials (for example TangoPlus or FullCure930), polyurethane foam (foam rubber), XPS foam, polystyrene foam, phenolic foam, styrenic block copolymers, polyolefin blends, elastomeric alloys, thermoplastic polyurethanes (TPU), thermoplastic copolyester, thermoplastic polyamides and the like. In one preferred embodiment, the valve filters are soft passive valve filters substantially made of polydimethylsiloxane (PDMS).

Said valve filters can have several shapes and sizes depending on experimental needs and the device design. For instance, they can be tightly-packed small posts of a soft polymeric material of e.g. triangular, polygonal, square or rectangular shape or can have a grid- or mesh-like appearance, adapted so that the filtering area (i.e., the area which a sample organism can pass through) is substantially non-parallel (e.g. perpendicular or slightly tilted) to the sample organisms' flow once pushed by a pressure pulse. Also alternative shapes can be envisaged such as a "half-moon" or "bean-like" shape, which is particularly convenient in case of selective filtering of every organism except roundshaped (spherical, elliptical, ovoid etc.) translucent organisms such as animal embryos or oocytes.

As said, the device is operatively connectable to means to directly or indirectly alter the pressure within the culture chambers and the reservoirs. The pressure applied can be a "positive pressure", i.e. when the applied pressure increases the internal chamber or reservoir fluid pressure, or a "negative pressure", i.e. when the applied pressure diminishes the internal chamber or reservoir fluid pressure, as in case of a suction. A means to apply a pressure will usually be coupled with the inlet or the outlet reservoir, either directly or indirectly (via e.g. a connection tube). Suitable means of altering the pressure within the device are external or integrated pumps or micropumps, combinations of capillary forces and electrokinetic mechanisms, hydrostatic pressure or simply a syringe. As will be evident for a skilled in the art, for what said above, the invention is intended to cover also a system comprising a microfluidic device as defined above and pressure means operatively connected to an inlet reservoir and/or an outlet reservoir adapted to generate a pressure within said inlet and/or outlet reservoir, in a way as to push its (their) content or at least a part of it.

Figure 3:
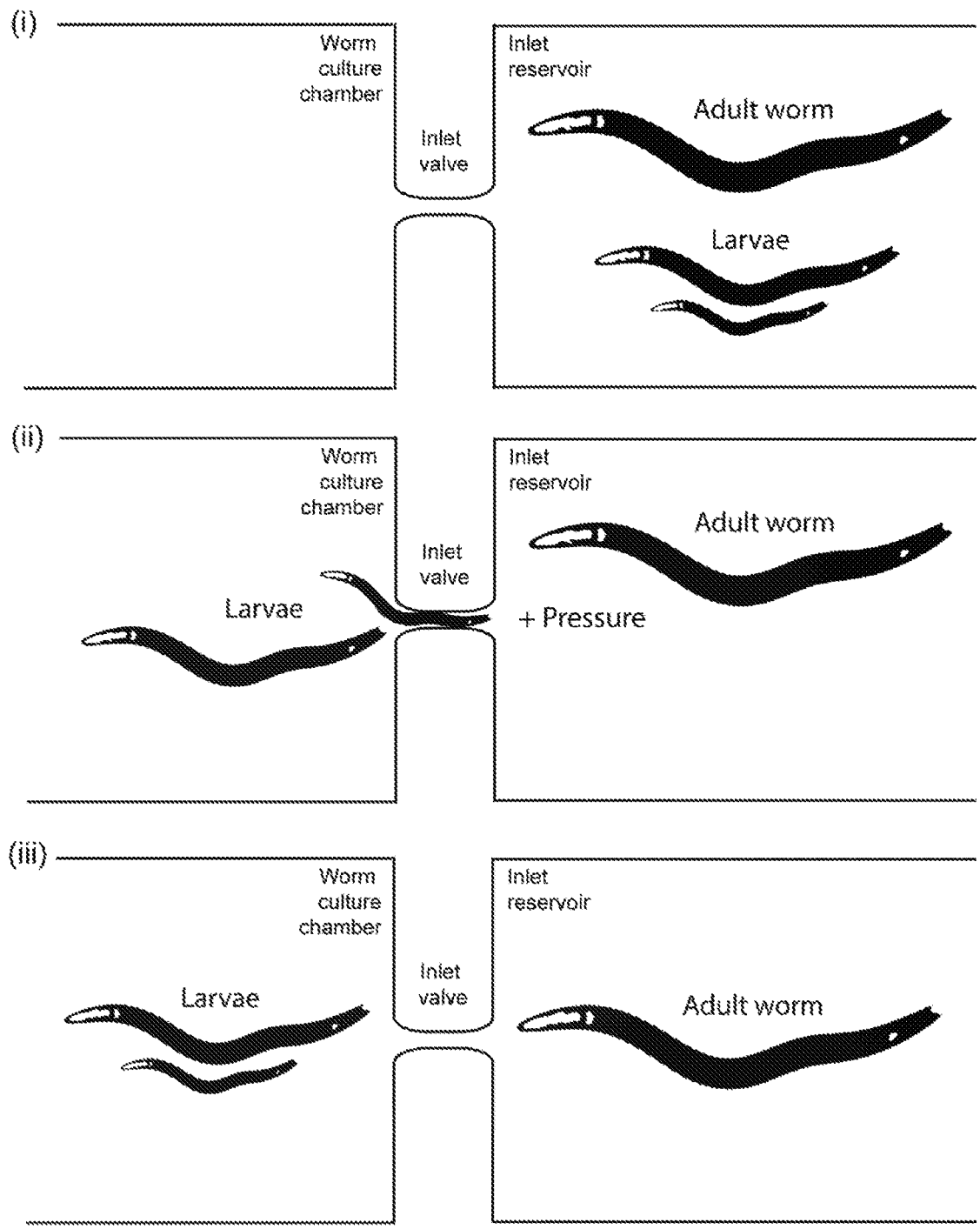
FIG. 3 depicts a schematic illustration of the size-dependent nematode selection by the worm-valve mechanism.

FIGS. 1 to 3 depict one exemplary and non-limiting embodiment of the invention and its features. FIG. 1 shows a diagram of the device of the invention using a worm as a model organism. The device has one inlet and one outlet reservoir connected with the central chamber through the valve filters. Said valves are selectively crossable since they allow fluid flow passage (of e.g. the culture medium), while preventing the worm to go from the inlet reservoir to the culture chamber. However, a pressure increase, such as a pulse pressure, can squeeze the worm through the inlet valve into the culture chamber (i), where the worm is then retained by the same valve mechanism. In this situation, the sample organism can be cultured and studied for a sufficient period of time depending on the experimental needs (ii). Another pressure increase can be used to extract the worm from the culture chamber, through the outlet valve in the outlet reservoir (iii). The worm and the culture medium are moved through the chamber and the reservoirs by introducing a pressure difference between its inlet and its outlet (e.g. by means of a syringe pump or by hydrostatic pressure).

FIG. 2 shows a detail of the inlet valve filter (i) and of the "worm-valve mechanism" (ii-iv). When the pressures in the fluid at the opposite sides of the inlet valve are essentially the same, or an eventual pressure difference is lower than a specific threshold, the worm cannot go from the inlet reservoir to the culture chamber (ii). When the pressure at the entrance of the inlet valve goes beyond a specific threshold, the worm gets deformed and become able to squeeze through the valve. Alternatively or additionally, if the material of the valve has an elastic character, this may deform under application of a pulse pressure, facilitating the entrance of the worm into the culture chamber (iii). Once the worm has entered the culture chamber, the pressure is removed, so that the worm is confined inside the chamber (iv). The same principle can be applied for transferring worms from the culture chamber to the outlet reservoir, through the outlet valve. The "worm valve" mechanism is merely controlled by the intensity of the flow passing through the filters and uses the elastic properties of the worm body and/or of the valve material or geometry. This mechanism is attributed to the following factors: exact geometry (cross-section, length) of the filter structure, the external pressure applied that causes instantaneous elastic deformation of the worm body (and/or of the valve itself) and the worm's swimming ability. A proper choice of the filter geometry can for instance ensure that worms of a desired age (e.g.: L1 larvae) can cross a passive filter valve only if the pressure difference between the two sides of the valve exceeds a certain threshold.

FIG. 3a shows a size-dependent worm selection. When a mixed worms' population is present in the inlet reservoir (i), a small pressure is sufficient for transporting smaller size animals through the inlet valve (ii), leaving behind a synchronized population of adults in the inlet reservoir (iii). Eventually, when all larvae are filtered out of the mixed sample, a procedure as illustrated in FIGS. 1-2 can be used to bring the adults in the culture chamber. The same principle can be applied for transferring worms from the culture chamber to the outlet reservoir, through the outlet valve. As a consequence, the device of the invention and the inventive worm-valve mechanism characterising it allow for a controlled passage of organisms of a specific size, depending. In present example, on their developmental stage. This gives the advantage, through a simple design, to ensure organism age synchronization for each experiment, even starting from mixed suspensions of organisms of different ages, thus also avoiding for instance, in case of worm nematodes, the usual bleaching step required to extract the eggs.

Furthermore, in certain embodiments, the filters can be used to extract worms at a certain larval stage from a chip (e.g.: L1 or L4) and transfer them to another chip, for transgenerational studies or continuous worm maintenance. The chips can be suitably operatively connected through e.g. tubular elements, or an intermediate passage of the worms through external reservoirs (or well plates) can be used for the chip-to-chip worm transfer.

A further possibility relies in the selection of sample organisms of different sizes, as well as of different ages when there is a correlation among size and age of the organism, by arranging different valve filters along the device. For instance, it could be imagined a device wherein the first filter valve allows the passage of the entire worm population from the inlet reservoir to the proximal chamber, the second filter allows for the passage of L1 and L2 larvae while blocking adult animals, the third filter allows for the passage of L1 larvae while blocking L2 larvae and so forth. In this way, parallel analyses on e.g. behavioural/phenotypic characteristics at different developmental stages of the sample organisms could be performed at the same time.

Still a further alternative is the possibility to synchronize a population of sample organisms, such as nematodes, as of the embryo stage: by using e.g. half-moon or bean-like shaped filters at the interface of the culture chambers, an operator could be able to wedge worm embryos, and possibly culture and characterize them, while eliminating all the rest of e.g. a mixed population. Once the embryos become L1 larvae, these can be cultured and/or filtered in other culture chambers for further studies. In such a way, the filtering structures work as an "embryo incubator array" for the isolation, imaging and/or phenotyping of individual embryos. This can also allow pursuing trans-generational studies from the first cellular divisions to the adult stage of several organisms in parallel by reiterating the process several times, through the simple optimisation of a protocol for the on-chip worm bleaching inside the culture chambers for isolating a highly synchronized embryo population in each chamber (FIG. 3b).

Figure 4:
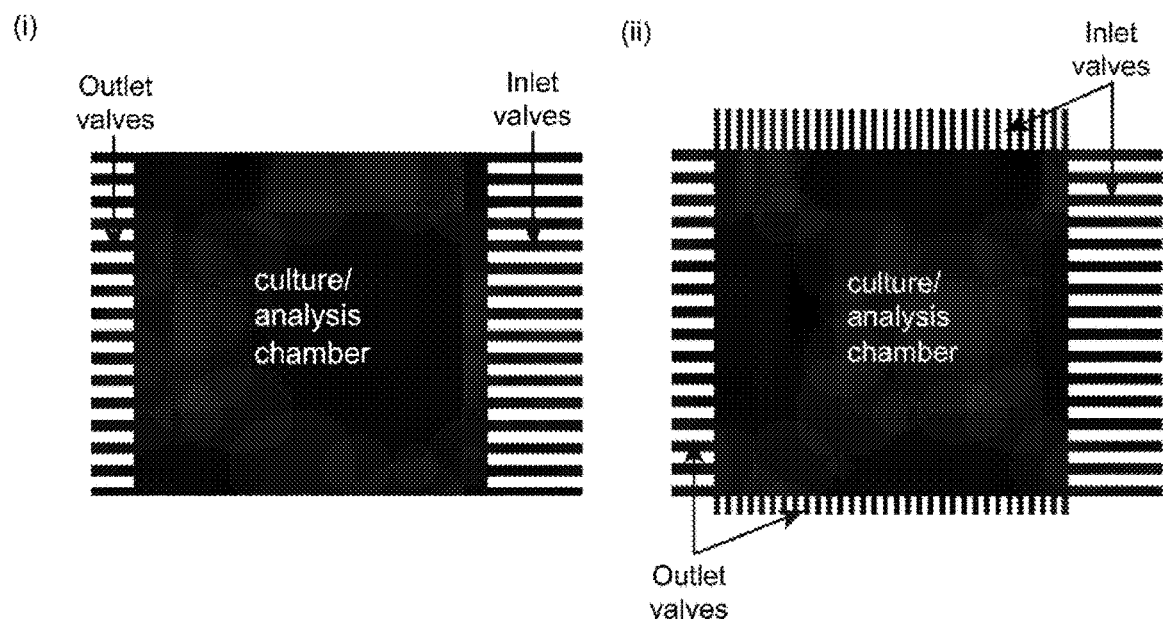
FIG. 4 depicts a schematic top-view of a square culture chamber with (i) multiple inlet and outlet valves and (ii) with a second set of inlet and outlet valves of smaller cross-section, which can be used for applying chemical compounds to the culture chamber, feeding the worms with bacteria or removing worms of smaller size from the culture chamber (e.g. worms' progeny).

FIG. 4 shows two of the possible alternatives for the filter valves of the microfluidic device. FIG. 4(i) is a top-view of a square culture chamber with multiple inlet and outlet valves. A second set of inlet and outlet valves of smaller cross-section, which can be used for applying chemical compounds to the culture chamber, feeding the worms with bacteria or removing worms of smaller size from the culture chamber (e.g. worms' progeny) is shown in (ii).

Figure 5:
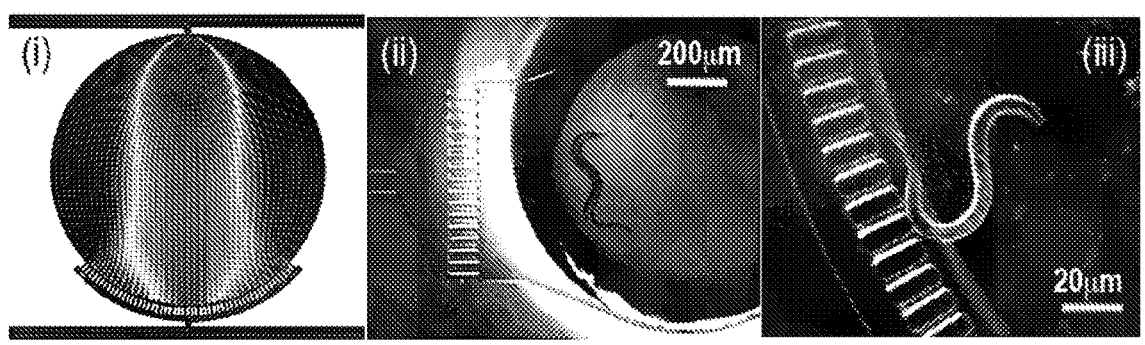
FIG. 5 depicts other embodiments of culture the chambers connected via worm-valves to microfluidic device's inlet and outlet reservoirs.

FIG. 5(*l*) shows a diagram of a disc-shaped culture chamber with one filter valve at the inlet and multiple filter valves at the outlet. FIG. 5(*ii*) shows a photograph of an inlet reservoir connected via multiple filter valves to a microfluidic channel. FIG. 5(*iii*) shows a photograph of a nematode larva in a part of the culture chamber schematically shown in FIG. 5(*i*).

Figure 6:
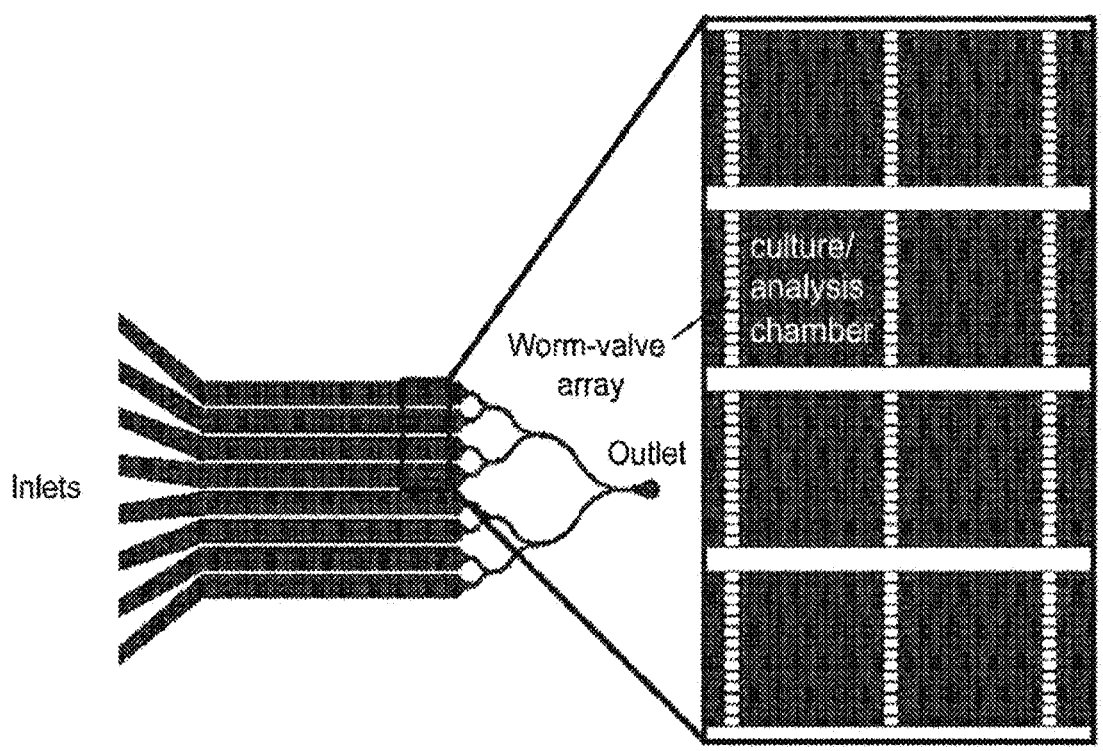
FIG. 6 depicts a schematic diagram of a microfluidic device consisting of an array of 80 culture chambers distributed along 8 adjacent channels and separated by multiple valve filters.

FIG. 6(*i*) shows a schematic diagram of a microfluidic chip consisting of a matrix of 80 culture chambers distributed along 8 adjacent channels and separated by multiple filter valves. In this chip, the pressure difference over the channels is obtained by applying a pressure at a single inlet/outlet, which can be used for filling the different culture chambers with a small number of worms and for providing the culture medium or possibly test compounds to the different culture chambers. By subsequent application of pressure pulses over the channels, the worm-valve mechanism allows the distribution of a discrete number of worms in the different culture chambers, as shown in FIG. 6(*ii*). In this scenario, the device can be used to carry on parallel analyses on worm populations under controlled conditions over each chamber or channel (e.g. for drug screening on the test organisms).

Figure 7:
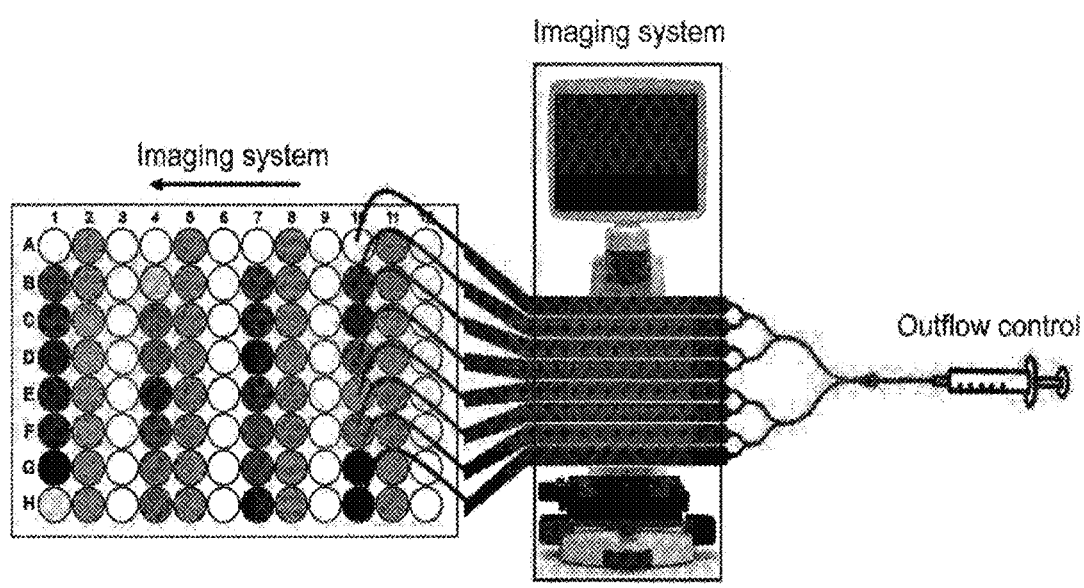
FIG. 7 depicts a schematic diagram of the microfluidic system of the invention.

The invention further relates to a system and a method for culturing and analysing a population of sample organisms. The system integrates the microfluidic device of the invention and exploits its unique features for running long-term cultures of multicellular organisms while studying their phenotypic and/or behavioural characteristics under different conditions. Said system comprises, apart from a system comprising the microfluidic device of the invention operatively connected to pressure means as previously described, at least a detection means arranged as to detect and possibly, at the same time, analyse specific parameters or phenotypic and/or behavioural characteristics of the sample organism. For instance, a light source can be arranged to illuminate the culture chambers of the device where one or a population of sample organisms is cultured, and a light detection means can be arranged to capture the light scattered or induced by the said organisms. In this embodiment of the system of the invention, any light source can be used to illuminate the culture chambers of the device integrated in the system. These includes, but is not limited to, white light, fluorescent light, infrared light, UV light, laser light, led light and even sunlight. A simple embodiment of the system of the invention relies in the microfluidic system as disclosed coupled with a microscope: the microscope light illuminates the culture chambers comprising the sample organisms, which can be seen and analysed through the microscope oculars (FIG. 7). Another simple alternative is the coupling of the microfluidic system with a camera as a detection means for e.g. recording the movement of the sample organisms for phenotypic/behavioural studies: in this alternative, even the sunlight can be a suitable meaning for illuminating the culture chambers. Multiple read-outs are envisageable for such a system, such as automated brightfield or fluorescent image analysis, computer-aided imaging via "worm-tracking" software and the like.

Further alternatives are envisageable vis-à-vis the detectors of the system of the invention, such as ad-hoc detectors for e.g. the detections of parameters like electrical measurements, chemical products measurements, temperature measurements and the like.

A great advantage of the system and methods of the invention relies in the possibility of complete or almost complete automation which can be achieved. This reduces experimental time and human intervention, as well as any issue related to that, including reduction of human bias and errors, ease of sample handling and data analysis, a throughput that is at least an order of magnitude faster than that by manual operation and so forth. Fluid flow, temperature, imaging, image processing, data treatment, further readouts (such as e.g. electrical, chemical, etc) and so forth, can be controlled via dedicated software and/or apparatuses for automated control of the platform. In at least some embodiments, for instance, the system of the invention can include an integrated temperature control system or an automated image processing code for direct data extraction upon imaging.

Example 1

Method for Screening Active Compounds by Using the Microfluidic System of the Invention Important advantages in terms of understanding the physiological effects of drugs may be taken by studying whole organisms during their development. *C. elegans*, as a model for many human diseases and for which many human homologous genes are known, is a potential candidate for clinical validation of drugs. Taking all the advantages of *C. elegans* as the organism of choice, such as the small size and ease to grow, the fact that many orthologues of human genes are known in its genome, its genetic manipulation is readily accessible and mastered, its developmental stages are well known and characterized and so forth, the inventors aimed at creating a platform enabling multiplexed drug screenings during the entire life-cycle of this nematode.

They used a micro-array approach to reach small-population resolution assay for high-content screening, eventually at high-throughput capability and with the possibility to automate the different steps of the analysis. In order to take as much advantage as possible from *C. elegans* studies at single-organism resolution, the inventors desired the microfluidic chip to give the possibility to:

injecting worm specimens in the chip;
making them grow from the larval stage to the adult age;
washing the progeny of the initial worms when they lay eggs;
administrating drugs at desired moments of the life-cycle.

This platform has also aimed to be used at different stages of the clinical validation of a drug: from screening a multitude of drugs for hit search, to tracing a dose-response curve for promising drugs, and finally to search for their targets. Inventors also wanted to approach a method to achieve single-worm resolution for the screens enabled by the chip.

To satisfy the above objectives, one has to be able to both feed the worms with *E. coli* and to get rid of the progeny during the egg-laying period of the adults, as well as to prevent cross-contamination of the different drugs and also to make a choice about the throughput one wants to achieve. A further issue was how to flow the nutrients and the drugs into chambers supposed to be isolated.

Inventors created a proof-of-concept model with the aim to find a screening method able to be run almost automatically and implementable at larger scale. The chosen method is perfectly scalable to higher throughput with minor modifications. A large effort has been faced to calibrate the instrument to be suitably fitted with some standards in drug screening science.

To enable high-content screens at high resolution, inventors have developed a microfluidic chip that selects the first larval stage (L1) of this animal. This chip is based on a micro-array approach and was fabricated by using standard soft-lithography: it is composed of several adjacent channels and separated into chambers by PDMS filter valves used for selecting the worms and to keep them in isolated small populations (1-10 worms per chamber). The channels are connected in a manner that enables the control of the feeding and the drug administration just by controlling the total outflow with only one syringe. The design of this platform and its operational modes highly improve automation possibilities, making it suitable to be used with any imaging system and for coupling with other standards in drug screening (e.g. automatic preparation of substances to administrate).

The final design of the chip is shown in FIG. 6. It consists of several channels (4 or 8) divided into chambers (10/channel) by small filters consisting of PDMS posts. Each inlet was plugged into a reservoir, and the outlet bringing to a syringe. This design is almost completely symmetric to try to assure as much homogeneity as possible to the fluids in the different paths: this increases the control of the flow rate. The geometrical features of the filtering channels were optimized (100 µm long, 8-12 µm wide) to select larval stages of $C.\ elegans$ and make them trapped into the chambers. Concerning the height of the structure, the parameters to be taken into account are essentially the size of the biological specimens to be inserted and the volume of the reagents to be injected. Other sensitive parameters involve the aspect ratio of the PDMS chambers/channels. After careful considerations, the value of 100 µm was chosen as a good trade-off.

The microfluidic platform has been used to directly select L1 worms from a mixed population. This would allow the avoidance of the bleaching step to extract the eggs. As a protocol, a mixed population was injected from the outlet of the chip until the desired amount of worms was reached before the first rank of filters, and then the liquid was injected at 10-20 µL/s with pulses of 1-2 seconds: the pulses at very high flow rate make the small PDMS filters between the chambers enlarge enough for a while to allow the L1 larvae to pass-through. This is made possible by exploitation of the hydraulic capacitance of the PDMS posts, which thanks to their aspect ratio (100 µm high, 70 µm wide), compress themselves during the pulses and restore their shape when flow stops. After 10-20 pulses, the chambers are filled with different populations of L1 larvae, with the general rule that chambers close to the outlet contain more worms than farther chambers. This is a good protocol to get L1 larvae from a mixed population, and allows to reach a much higher resolution with respect to standard tests on agar plates (1 to 10 worms per chamber on average). The worms trapped could not escape from the chamber just by swimming nor for flow rates lower than 200 nL/s: this was therefore, for this particular setting, an upper limit for the flow rate to be used for feeding and drug administration.

When the worms are adults and lay eggs, the same protocol after hatching can be used to wash away the new larvae, remaining with the same worms in the chamber from the beginning to the end of their life-cycle eventually.

A fundamental aspect of the chip is the prevention of the cross-contamination between chambers of different channels, which are supposed to screen different drugs or different concentrations of a drug. The most automatable and manageable solution that was found was to have an imposed flow rate for several fluidic paths by using only one syringe. The proposed design makes it possible by the fact that in these conditions the Reynolds number and the Péclet number are very low and very high, respectively, and therefore the mass transport occurs essentially by advection. Numerical simulations have been performed to get an estimation of the effects of this phenomenon and it was found that good flow rates to avoid cross-contamination should be higher than 1 nL/s at the outlet.

Figure 8:
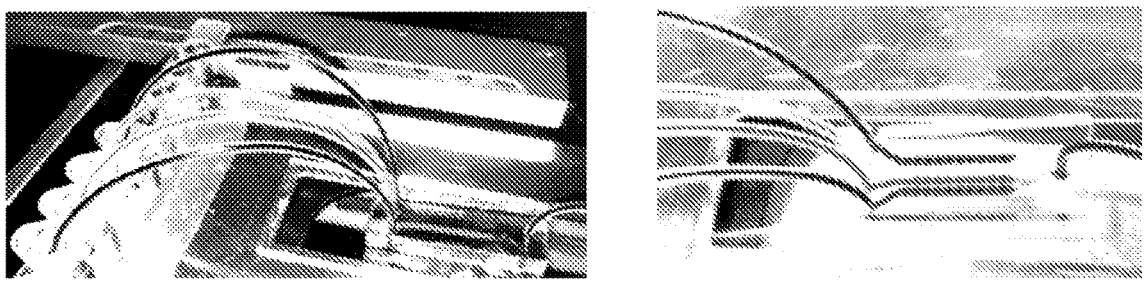
FIG. 8 depicts a chip configuration with ink.
Figure 9:
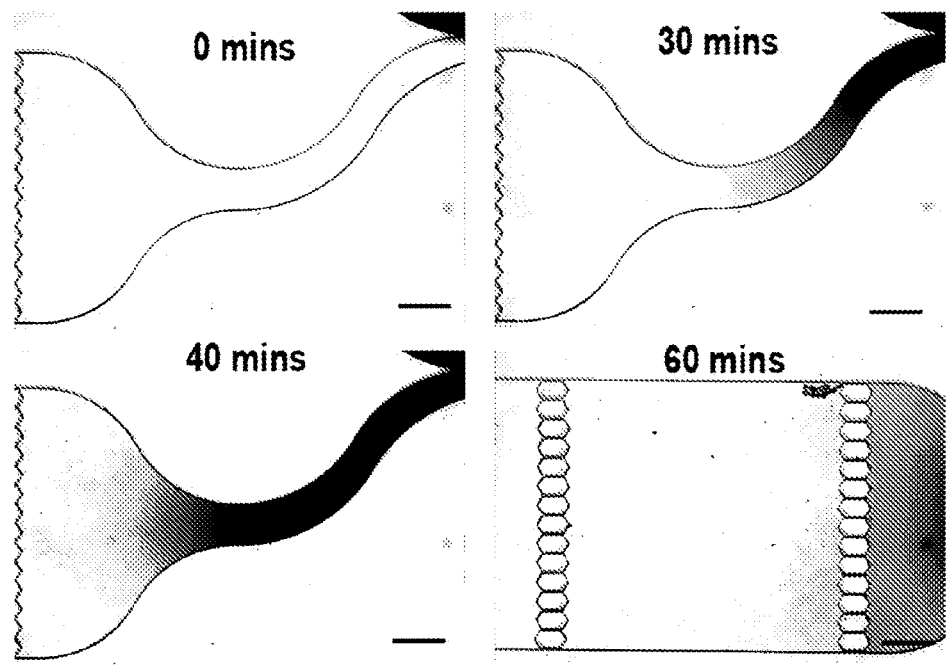
FIG. 9 depicts the diffusion of ink into the adjacent channel, for several time-lapse after stopping a 4 nL/s outflow.

This behaviour has been tested experimentally by using inks of different colours on chips with 4 inlets. Each inlet has been plugged to a reservoir containing the ink (FIG. 8), and sucked with a syringe from the outlet at several flow rates. Results show that when decreasing the outlet flow rate, the 4 different inks coming from the different inlets tend to mix because of increasing diffusive mass transport (not shown). But it can also be concluded that for a total outflow of 4 nL/s (corresponding at about 1 nL/s flowing in each of the 4 channels), there is no back diffusion of the fluid from the several paths, which is in agreement with the simulated fluidic behaviour. To further quantify the diffusion phenomenon in the chip, it has also been studied the behaviour of the ink diffusion after completely stopping the flow. Serial pictures at different time after stopping a 4 nL/s outflow have been taken (FIG. 9). The diffusion is very slow and it takes about 1 h to have a visible change in ink concentration in the first chamber of the adjacent channel.

In order to have a more precise evaluation of the back diffusion of a drug into the several channels, an experiment similar to the one with the ink has been performed, but this time it was used 1 mM fluorescein (1 mM) in one of the channels and water in the others. The fluorescence intensity has been monitored in the 4 antichambers (1 per channel) that were closer to the outlet over time for a total outflow of 1 nL/s. A time-lapse image shows no cross-contamination within more than 3 h of study even at a very low flow rate of 1 nL/s. The same chip ran overnight at the same flow-rate, and the following morning no cross-contamination was observed.

An issue in the drug administration protocol, in particular for long screens involving several larval stages, is to provide $E.\ coli$ together with the drug for feeding the nematodes. This is a main stake because when administrating drugs, cross-contamination of the different channels should be avoided, which would interfere with the screen. As observed, for high enough flow-rates this is not a problem, because the fluidic paths stay well separated. But maintaining high flow-rates for long time would consume a large amount of drug, which is normally very expensive. The inventors therefore wanted to find a protocol to optimize, at the same time, the feeding with $E.\ coli$ and the drug administration. $E.\ coli$ can be readily perfused into the chip even at flow rates as low as 4 nL/s. To be sure to avoid cross-contamination, but aiming to consume as less volume of drug as possible, it has been chosen to administrate the drug together with $E.\ coli$ in a continuous-perfusion mode by sucking at 4 to 8 nL/s with a syringe. In order to evaluate the flow-rate of the individual channels relative to the total outflow imposed, it was measured for each channel the time to empty 300 µL-wells: these were found to be equal within a 6% range.

Since with the microfluidic chip of the invention it is possible to screen during the whole life-cycle of $C.\ elegans$, it is of high interest to find a solution to automate the protocols, to allow reproducibility and even to envisage the coupling with other standards in drug screening. A 8-channel chip is perfectly adapted to multiplexed and serial screens.

One can imagine complex screens that would require to sequentially provide C. elegans with several substances:

Target search: 1st, knock-down of desired genes by RNA interference; 2nd, drug screening; 3rd, washing; 4th, knock-down of other genes by iRNA; 5th, drug screening; 6th, washing; etc.

Combination of drugs administered at different developmental stages: 1st, screening of first drug at L1; 2nd, washing; 3rd, screening of second drug at L2; 4th, washing: etc.

Importantly, the standard protocols for drug screening in wells completely prevent the possibility to wash out substances. The system will therefore certainly enable much more flexibility to study drug-induced response of all the different stages of C. elegans specimens. Furthermore, with this chip that perfectly fits any stage used with glass slides, there will be no more need of expensive "black-box" machines for automatic recording of the signal: any laboratory will eventually have the possibility to choose the most suitable imaging system.

One of the big advantages of the system of the invention is the possibility to screen several drugs/concentrations/targets in parallel by using only a syringe. The protocol can therefore be divided into steps of different duration, during which the syringe moves at different speed. This allows the continuous perfusion necessary to feed the worms and to prevent the cross-contamination during drug administration. Thanks to programmable valves one can also automatically and rapidly empty the syringe when it is completely filled. The syringe can thus undertake several runs of sucking for the same screen without any operator intervention. Nowadays, many automate protocols and robots enable to prepare 96-well plates in a high-throughput manner with given substances to be screened. Seeking for interfacing with such standards inventors have used as reservoirs for the screens the well-strips taken from a 96-well plates.

To demonstrate the advantage to have few nematode specimens in a chamber, many chambers to increase the statistics, and several channels to test different concentrations, it has been designed a motility assay able to be performed in real-time and with a very wide field-of-view. Several concentrations of a drug called tetramisole, which is known to paralyze the worms, have been used. The aim of the experiment was to correlate the concentration of the drug with the number of paralyzed worms over time, and to trace a dose-response curve for this drug.

L1 specimens of wild-type C. elegans have been injected in the chip with the above-described protocol and fed them for 2-3 days to get adult worms. Serial dilutions of tetramisole were prepared in the 200 µL wells of a 12-wells strip. The wells were plugged in the inlet and sucked with a syringe from the outlet at total outflows between 100-200 nL/s for 40-80 minutes. The procedure was recorded in real-time for all the chambers at the same time by using a stereo-microscope. It was used a suitable ring-shape back-illumination to enhance the contrast and make the adult worms much lighter than the background.

Image analysis was done afterwards directly on the video recorded: the number of paralyzed worms per chamber were counted every 10 minutes from the beginning of the drug injection, and the total percentage of paralyzed worms per channel (1 channel=1 concentration) was calculated. As the literature proposes, the worms were considered as being paralyzed when they displayed coiling or no movement at all. A main advantage of the chip with respect to standard screens in agar plates or wells, and that increases the reliability of the motility screen, is that the liquid is continuously perfused in the chip. This means that:

the drug concentration accessible to the worms in the chambers remains constant during the whole screen;

the worms are stimulated by the flow, which induces them to move; this prevents from considering as paralyzed a worm that does not move only because it is at rest.

Figure 10:
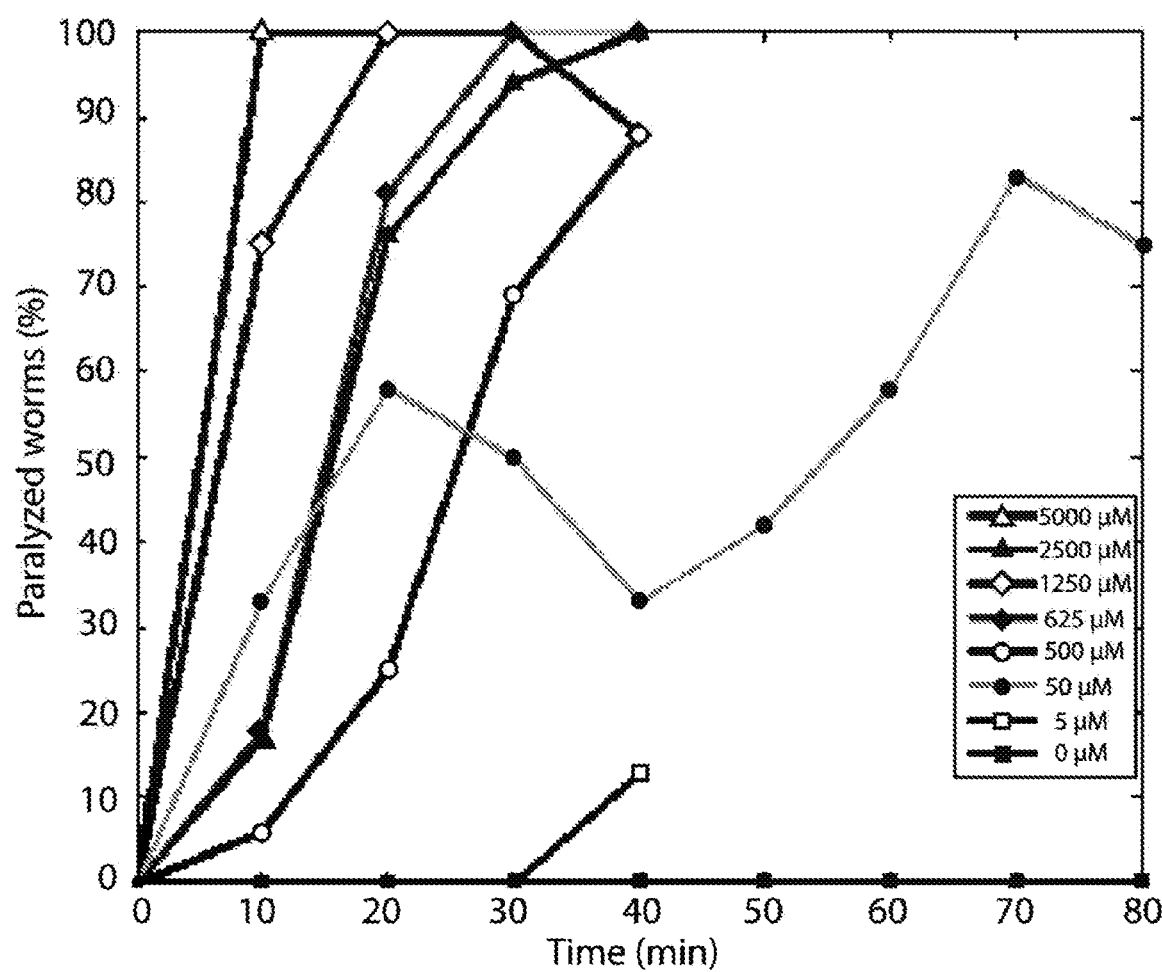
FIG. 10 depicts the results from tetramisole screen. Top, response versus time for several concentrations tested; bottom, dose-response curve traced with the average value of paralyzed worms between 30 and 40 minutes after tetramisole injection. The numerical values of the parameters from a sigmoidal fit are shown in the legend.
Figure 10:
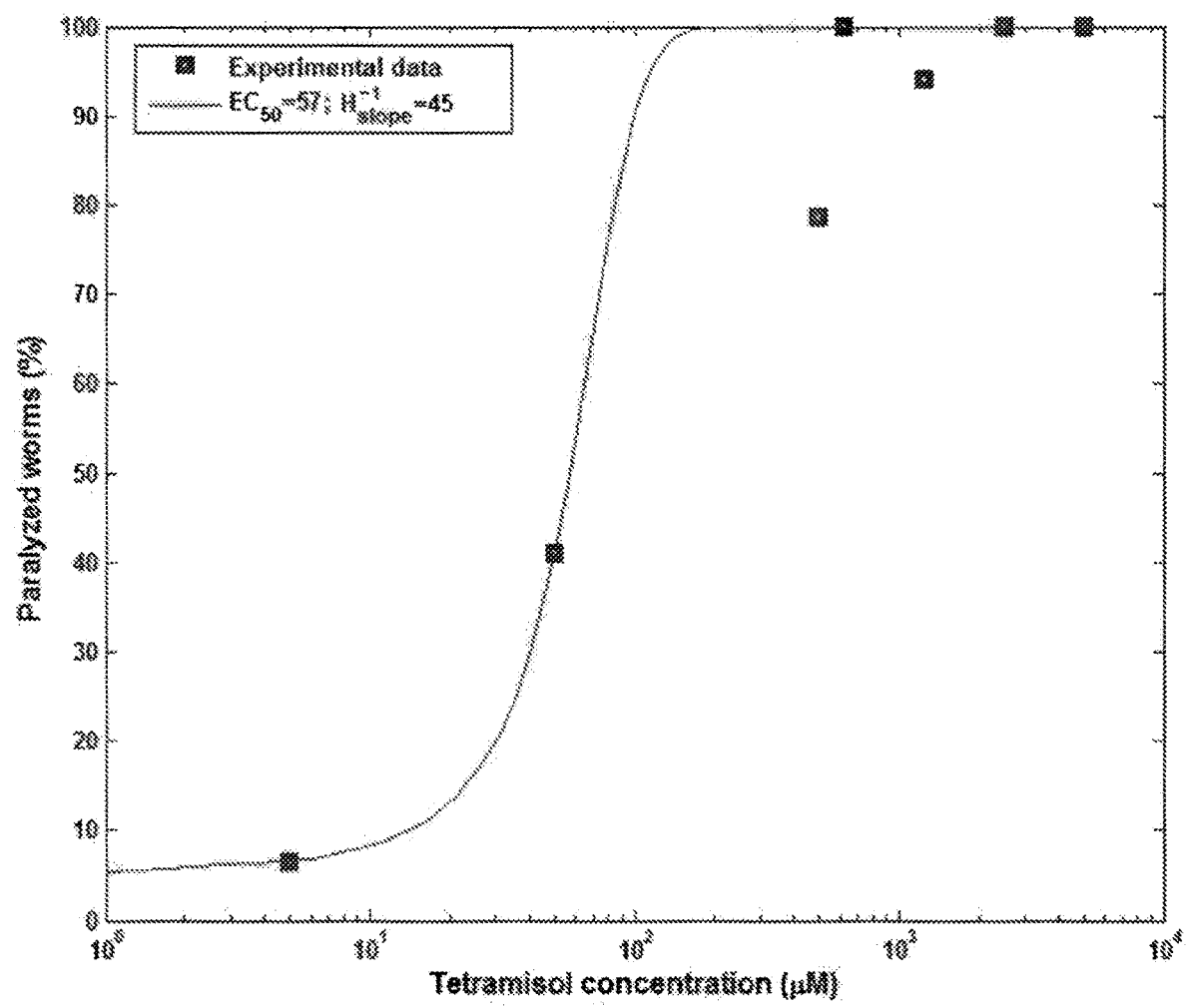

Results for the concentrations tested are shown in FIG. 10. As can be seen, there is a strong correlation between the amount of tetramisole administrated and the response-delay of the nematodes. A particular behaviour was observed for the 50 µM concentration, which initially seems to be more effective than the higher concentrations, but which does not have an always increasing effect. This could be due to the fact that given the not very large number of worms in the channel for this concentration (13 specimens in total), even a difference of 1-2 worms when counting the paralyzed ones can change the percentage value to 15%.

We also traced a dose-response curve for this drug by using the value of the mean percentage of paralyzed worms between 30 and 40 minutes after tetramisol injection FIG. 10. By fitting this curve with a sigmoid function:

$$y = \frac{100}{1 + 10^{H_{slope}(EC_{50} - x)}}$$

an $EC_{50}$ value of about 57 µM and a Hill slope of about 0.02 µM was obtained. This screen has been performed with two 4-channels chips, but with a 8-channels chip, as it still fits with the optics of current stereo-microscopes, one can test up to 7 different concentrations at the same time, by highly decreasing the delay for obtaining a complete dose-response curve.

Example 2

An Automated Microfluidic Platform for C. elegans Embryo Arraying, Phenotyping, and Long-Term Live Imaging For living organisms, environmental conditions to which they are subjected during the embryonic phase are crucial for their later development. Caenorhabditis elegans is an attractive model organism for embryogenesis studies, as embryos develop over a matter of only hours. So far, research was based on tedious manual handling protocols so that precise analysis of populations at single embryo resolution were impossible. Studies of the real-time dynamics of embryonic development require a gentle embryo handling method, the possibility of long-term live imaging during the complete embryogenesis, as well as of parallelization providing a population's statistics, while keeping single embryo resolution. The inventors describe an automated approach that fully accomplishes these requirements for embryos of C. elegans. The developed microfluidic platform makes use of pure passive hydrodynamics to run on-chip worm cultures, from which synchronized embryo populations can be obtained, and to immobilize these embryos in incubator microarrays for long-term high-resolution optical imaging. The method can be generally used for protein expression and developmental studies at the embryonic level, but can also provide clues to understand the aging process and age-related diseases in particular. The microfluidic platform not only allows automatic selection of adults from a mixed worm population and their subsequent culture on-chip, but also permits automatic capture and study—under perfectly controlled conditions—of the embryos they lay.

Fabrication of the Microfluidic Chip

Microfluidic devices were prepared by soft lithography using 2-layer SU-8 molds. Briefly, conventional photolithography was used to pattern a 35 µm-thick layer of SU-8 photoresist on 4-inch wafers. A 85 µm-thick layer of SU-8 was then patterned on top of the first one. The silicon mold was then diced in 15 mm×18 mm microchips, which were inserted at the bottom of an aluminum/polymethylmethacrylate (PMMA) mold for PDMS casting. 1.5 mm diameter steel pins were used to define the lateral connections of the device for the external tubing insertion. A liquid PDMS mixture (10:1 base:cross-linker weight ratio) was degassed, injected into the mold and cured at 100° C. for 1 h. Upon extraction from the mold, each PDMS chip was bonded by plasma-activation to a 150 µm-thick glass coverslip. The chip was then connected to external tubing and enclosed in a PMMA holder (FIG. 11a), designed for the observation of the device through any upright or inverted microscope and with any kind of objective.

System Control and Microfluidic Device Operation

A live-cell microscopy environmental control system (Visitron, Puchheim, Germany) allowed controlling the chip temperature over the whole duration of each experiment. The microfluidic operations were controlled using Nemesys syringe pump control software (Cetoni, Korbussen, Germany). Experimentally, the microfluidic chip was first filled with Pluronic F127 solution, incubated for 30 min inside the device, to prevent $E.$ $coli$ sticking and accumulation inside the microchannels. Few worms from a non-synchronized population were suspended in 10 µL of M9 buffer and sucked in a microfluidic tube, which is then connected to the device. From this point on, the system is completely controlled by software, through the automated sequential steps described in FIG. 12.

Automated Operation of the Platform

Figure 12:
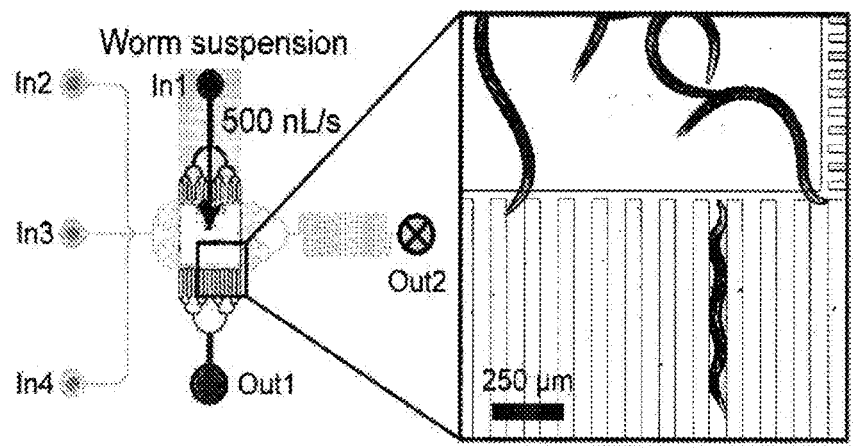
FIG. 12 depicts an operation mode of one embodiment of the microfluidic device. (a) First a 10 μL suspension of worms in M9 buffer is injected into the microfluidic device along the In1-Out1 direction at a flow rate of 500 nL/s. Symbols used for the in- and outlets: dot and arrow=syringe in use (e.g. In1); dot=syringe not in use (e.g. In2); circle=open valve (e.g. Out1); cross and circle=closed valve (e.g. Out2). The "worm synchronization filter" is tailored to retain inside the chamber only adult worms, as selected by their larger size and their better swimming abilities (see picture in zoom). (b) Subsequently worm culture is controlled by periodically injecting *E. coli* in M9 buffer along the In2-Out2 direction, typically at 50 nL/s flow rate. This ensures normal development of the worms in the liquid environment and continuous embryo production during their adult life span (see picture in zoom). Optionally, drugs or chemicals can be introduced at the In4 inlet for on-chip worm treatment. (c) Injection of M9 buffer at 200 nL/s flow rate along the In3-Out2 direction triggers the transfer of all the eggs present in the chamber towards the incubator array, where they are captured by passive hydrodynamics, as shown by the superposition of 13 video frames in the zoom. (d) The perfusion of *E. coli* suspension towards both Out1 and Out2 simultaneously ensures proper worm feeding inside the culture chamber and stable embryo positioning inside the incubators, enabling parallel time-lapse imaging of the embryos at cellular resolution (see picture in zoom).
Figure 12:
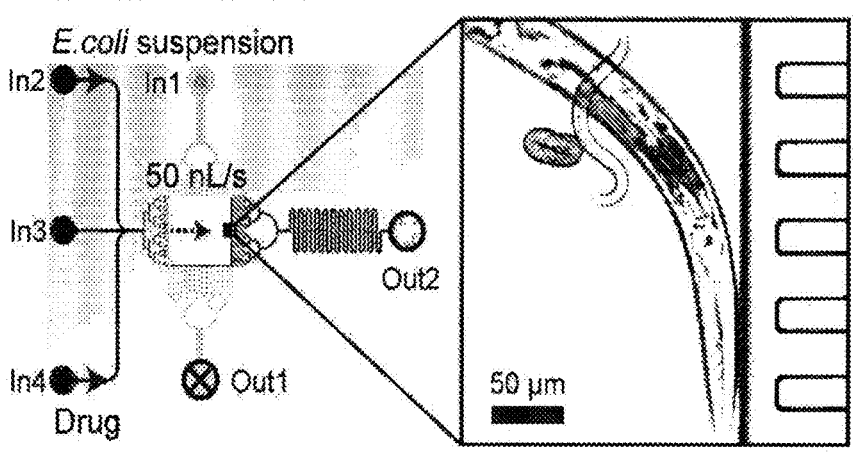
Figure 12:
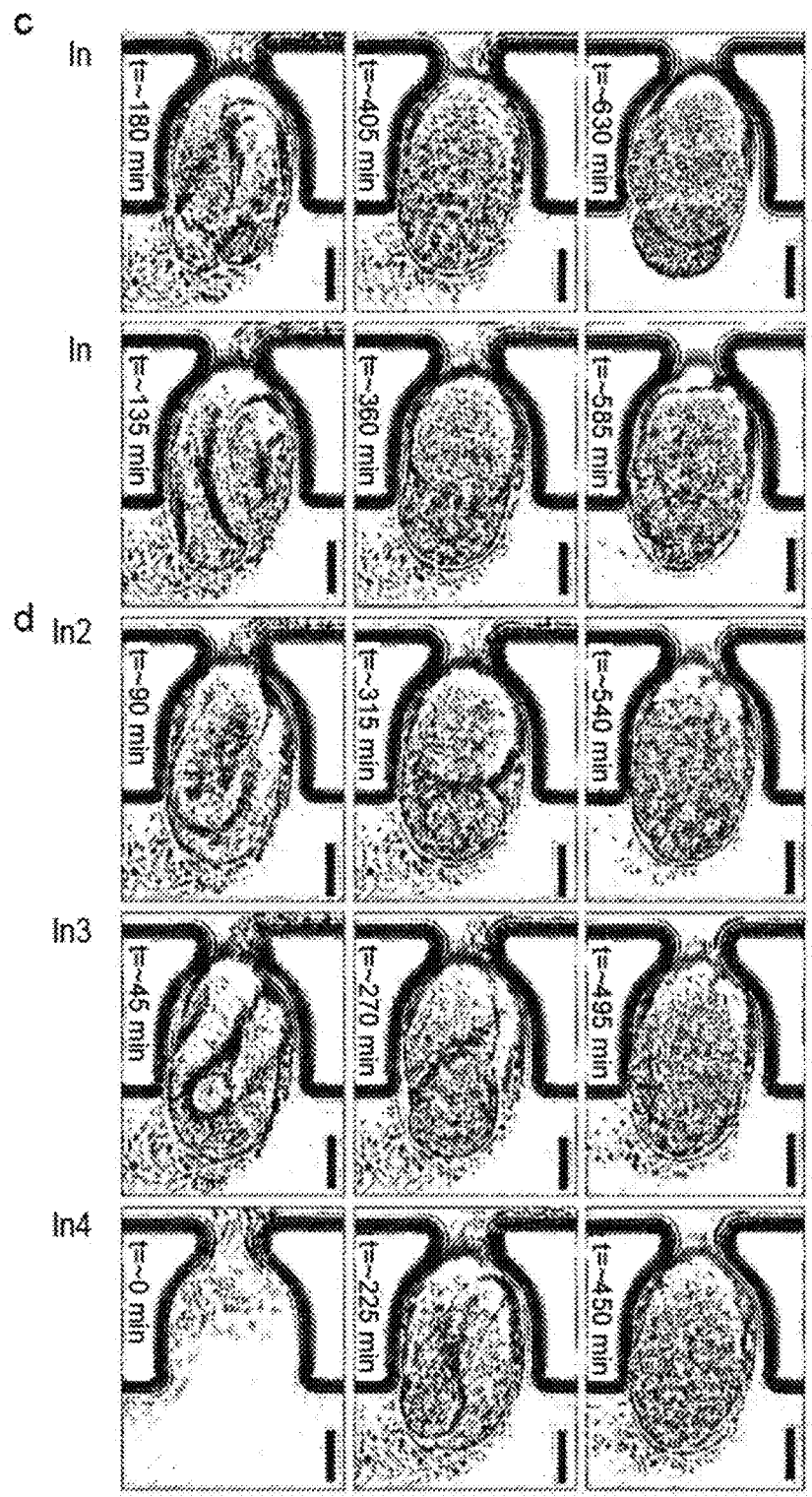

In each experiment, worms and embryos are manipulated via sequences of fully automated operations (FIG. 12). A worm suspension is first injected into the microfluidic device through the top port (In1 of FIG. 12a) and directed towards the "worm synchronization filter" by opening the valve at "Out1". The geometry of the chip is optimized for retaining inside the worm culture chamber only adult worms by simply selecting the correct flow rate for the sample injection. In practice, at a flow rate of 500 nL/s, in a few tens of seconds, all the larvae present in the suspension are directly washed out of the chip, while adult worms are kept inside the chamber both due to their larger size and their better swimming abilities/resistance against the flow (zoom of FIG. 12a). Alternatively, a L1-L4 larvae suspension can be injected at a flow rate of 100 nL/s to retain just L4 larvae inside the chamber. Eventually, the number of captured worms can be adapted by running an optional "washing step", where M9 buffer is injected for a few seconds along the In1-Out1 direction at higher flow rates (1 to 5 µL/s). Upon isolation of a defined worm population inside the chamber, worms are cultured and can be eventually treated on-chip with specific drugs or chemicals (FIG. 12b). For worm culture/treatment, an $E.$ $coli$ suspension is injected in the chamber at a desired rate, through the In2-Out2 direction, while drugs or chemicals can be introduced in the chip at controlled concentration and precise instants of the worms' lifespan. A simple increase of the flow speed inside the chamber along the In3-Out2 direction is then used to transfer the eggs present in the chamber towards the embryo incubator array. In practice, a 200 nL/s flow of M9 buffer allows recovering all the eggs present in the chamber and isolating each of them in a single micro-incubator via passive hydrodynamic trapping up to complete array filling (FIG. 12c).

Parallel time-lapse imaging is then started, either for the full array or by scanning each individual embryo at high resolution, at desired frame rate, magnification and light wavelengths, depending on the analysis of interest (FIG. 12d). During live imaging, a slow flow 5-10 nL/s of M9 buffer is applied along the In3-Out2 direction to assure stable positioning of the embryos in the array. Optionally, for sequential studies on embryo populations produced by the same worms at different periods of their full adult lifespan, worm culture can be maintained in the chamber by the perfusion of $E.$ $coli$ from In2 inside the chip. Both the valves at Out1 and Out2 are left open in this case, and the different hydrodynamic resistances of the two orthogonal directions result in a partitioning of the flow between the two outlets, with most of the liquid flowing through Out1. This establishes a slow flow through the incubator array, ensuring stable positioning of the embryos over long periods, while still reducing $E.$ $coli$ accumulation in the array area, which could compromise the results of embryo fluorescent imaging, because of the autofluorescence of $E.$ $coli$ bacteria.

Image Acquisition and Processing

The microfluidic chip was integrated onto an inverted microscope (Axio Observer, Zeiss) equipped with two illumination systems: (i) a precisExcite High-Power LED Illumination system (Visitron, Puchheim, Germany) for brightfield imaging and (ii) a Lambda DG4 illumination system (Sutter instruments, Novato, CA, USA) for fluorescence imaging. The microscope had a motorized xy-stage, equipped with an ASI piezo controller for z displacement (Visitron, Puchheim, Germany) and the automated imaging process was controlled using VisiView Premier Image acquisition software (Visitron, Puchheim, Germany). To start the automated imaging process, the position of the first egg in the array was set as initial point of the xy-stage scanning, while the locations of the other eggs were automatically determined by the interdistance between adjacent incubators (118 µm). A "wavelength program" was set on the software, to automatically switch between brightfield and fluorescent imaging modes, by controlling both the illumination systems. "Time-lapse" and "stage position" programs were set to automatically perform scanning and imaging over the full array at a desired rate, hence resulting in parallel time-lapse imaging of all the embryos. To avoid phototoxicity effects during these fluorescence imaging experiments, the exposure time of the embryo to the fluorescent excitation light (t<100 ms) was minimized and pictures were recorded at a single focal plane of the microscope (i.e. at a single z value), despite the possibility of taking z-stacks with our setup. The movement of the embryo inside its eggshell during the twitching phase could sometimes introduce instantaneous modulations in the collected fluorescent intensity, because of the time-dependent positioning of the developing larva inside the focal volume of the microscope objective, but variations of the average fluorescent intensity of the embryo in a given xy-plane remained relatively small. A simple Matlab script (MathWorks, Natick, MA, U.S.A) was written to reorder the large amount of data of each experiment according to the image xz-coordinates, time, light wavelength and exposure time. Image processing was performed with Fiji software.

Platform Design and Automated Operation

Figure 11:
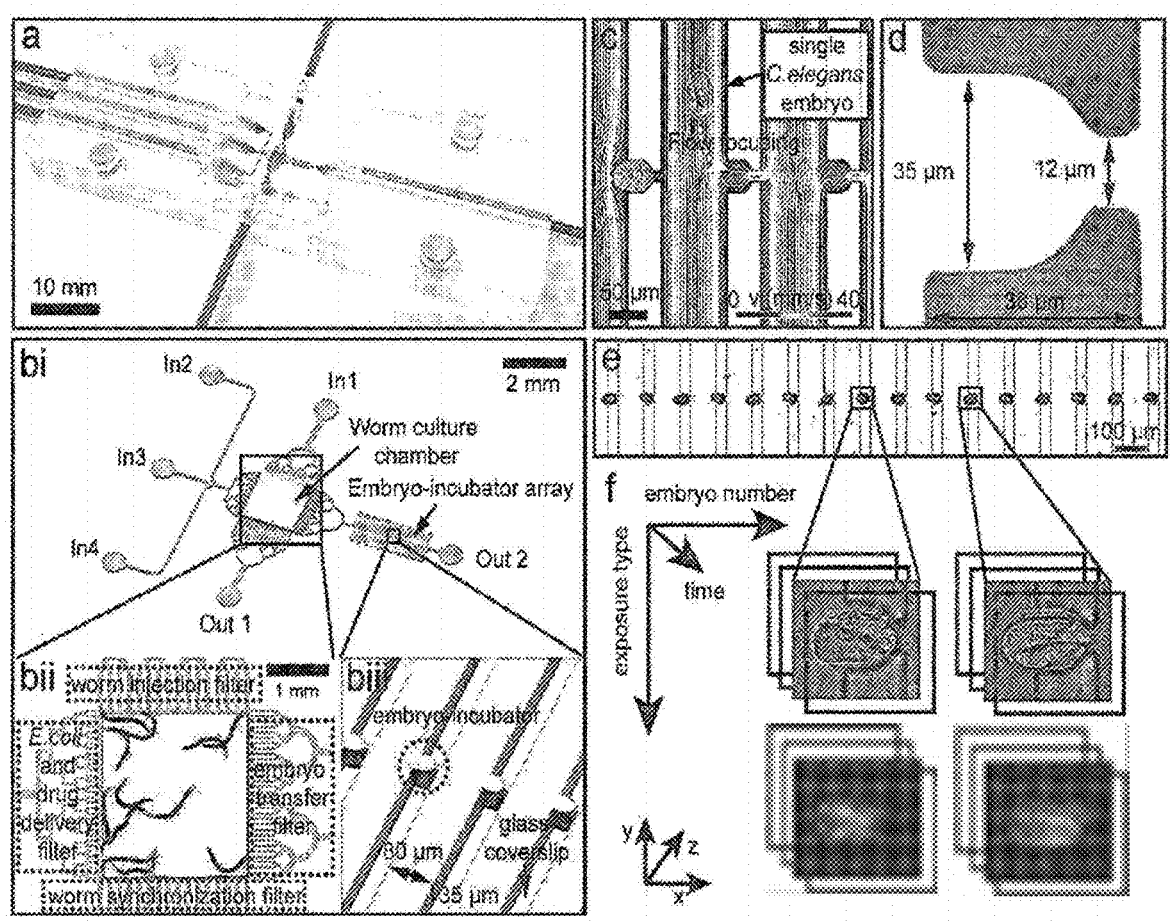
FIG. 11 depicts an overview of one embodiment of the microfluidic device. (a) Picture of the microfluidic device, sizing 25 mm×75 mm (standard microscope slide size), including lateral microfluidic connections, which make the device compatible for imaging with every upright or inverted microscope. (bi) Schematic representation of the central part of the microfluidic chip, having as main constitutive parts: the worm culture chamber, the embryo-incubator array, four inlets (In1 to In4) and two outlets (Out1 and Out2). (bii) Zoom on the worm culture chamber, including a drawing of young adult *C. elegans* for size comparison. The chamber is delimited by specific microfluidic channel arrangements, tailored for different functions: worm injection, worm synchronization, *E. coli*/drug delivery and egg transfer. (biii) Three-dimensional schematic zoom on a portion of the embryo incubator array. (c) Finite element method simulation (Comsol Multiphysics) of the fluid dynamics in the incubator array region, showing the principle of passive hydrodynamic arraying of single embryos. Fluidic velocity and streamlines are calculated for a flow rate of 100 nL/s at the inlet In3. (d) Micrograph of a single incubator on the SU-8/silicon master mold used for PDMS casting. (e) Micrograph of a section of the array with immobilized embryos. (f) Illustration of the multi-dimensional imaging that is enabled on the array of embryos and spans six dimensions: the 3 spatial coordinates, time, exposure type and embryo number in the array.

The robustness and automation of the system completely relies on passive hydrodynamics, with no need of any active component on-chip, such as integrated valves. This approach allows simplifying fluidic protocols and significantly minimizing fabrication constrains of the device, which simply consists of a monolithic polydimethylsiloxane (PDMS) microfluidic chip, sealed to a ~150 μm-thick glass coverslip. The microfluidic chip features two main components: a "worm culture chamber" and an "embryo-incubator array" (FIG. 11a,bi). External flow control through four independent inlets is achieved via computer-controlled syringe pumps, while two external valves are used to open and close two separate outlets. The worm culture chamber is delimited by specific microfluidic channel arrangements for generating uniform flow distributions in the chamber and for filtering entities of different size (FIG. 11bii): a "worm injection filter", for gentle insertion of mixed worm suspensions into the chamber; a "worm synchronization filter", to select the age of the worm population to be tested, by only retaining either adult worms or L4 larvae inside the chamber; an "E. coli/drug delivery filter", to homogeneously introduce feeding and treatment solutions inside the chamber; an "embryo transfer filter", to reliably displace embryos from the chamber to the embryo-incubator array upon egg laying. The embryo-incubator array consists of a serpentine channel in which each pair of branches is connected by isolated micro-compartments, specifically tailored for the trapping of C. elegans embryos and their high-resolution imaging through the glass coverslip (FIG. 11biii). Embryos, which are transferred to the embryo-incubator array are automatically positioned in the micro-incubators by passive hydrodynamic trapping (FIG. 11c). The design of this section of the chip is optimized according to both general microfluidic rules and specific needs related to the characteristics of C. elegans embryos. Overall, the fluidic design results in enhanced efficiency of capture and stable positioning of single embryos, with unprecedented performance in terms of control and reliability of the trapping mechanism for non-spherical objects. The flow rate distribution inside the array has to ensure the capture of a single embryo for each micro-incubator. Since the number of available embryos is being limited by the egg production inside the chamber, a perfect efficiency of the hydrodynamic trapping method has to be established in order to recover all eggs. At the same time, however, high trapping efficiency is typically associated to higher fluidic pressures through the micro-incubators. Therefore, forces exerted on the incubated eggs have to be considered as well, to prevent the flow from introducing undesired mechanical stresses on the captured embryos.

A crucial role for the system performance is clearly played by the geometry of the micro-incubators, hence different types of microincubators have been fabricated and tested. For high-resolution parallel time-lapse imaging of the whole embryo population and automated image processing, all the embryos have to be perfectly arrayed in stable positions and kept correctly aligned and well-oriented for several hours. The incubator size and shape were optimized mainly according to these needs, with a final design featuring elongated semicircular incubators, which are 35 μm wide, 38 μm long and 35 μm high (FIG. 11d). Using these dimensions, single embryos can be reliably positioned and aligned inside the incubator array (FIG. 11e). The whole incubator array features 20 micro-incubators, which are progressively filled by embryos as soon as they are naturally laid. This number is chosen to provide a significant data statistics for each experiment, while still maintaining a good level of age-synchronization among all the embryos in the array. For a worm culture, which is at the peak of its egg production, complete filling of the incubator arrays typically takes around 1 hour. The whole embryo population is then studied using fully automated multi-dimensional imaging, covering six independent dimensions: the 3 spatial coordinates, the development time, the exposure (brightfield, fluorescent) duration, and the embryo number in the array (FIG. 11f).

Automated Analysis of Embryonic Morphogenesis

Figure 13:
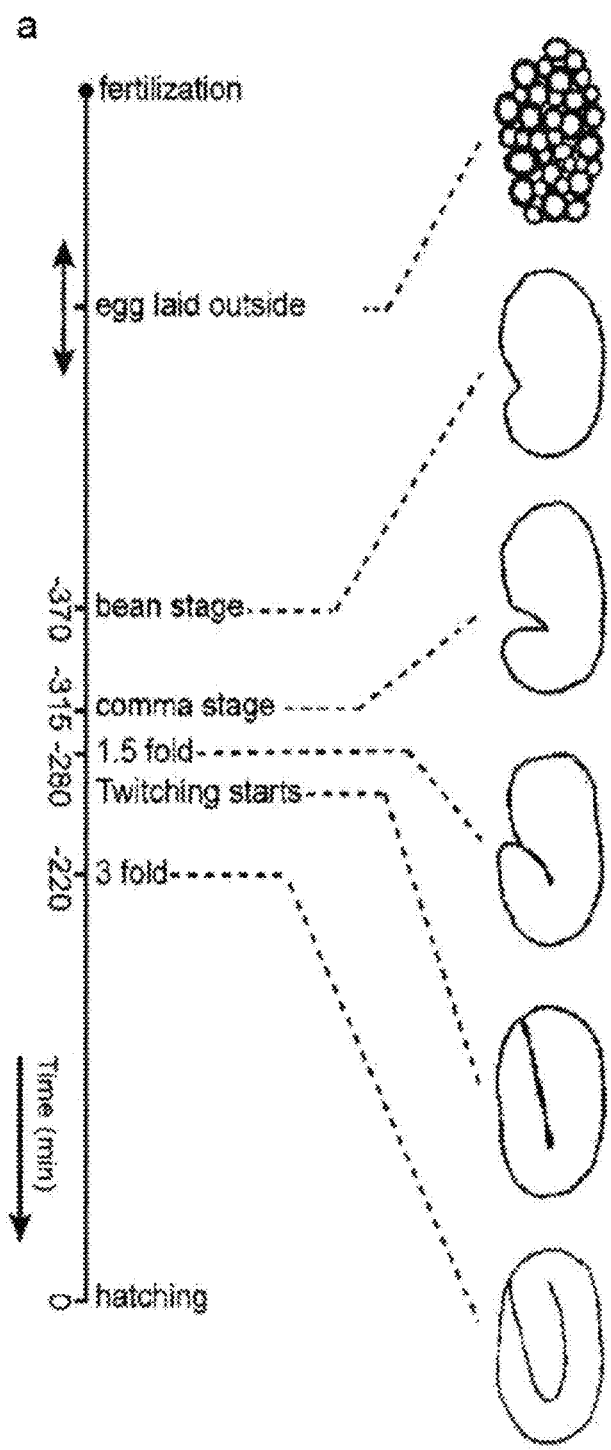
FIG. 13 depicts a study of *C. elegans* embryogenesis. (a) Time-lapse of the main embryonic stages of development with typical time indications for T=25° C. and wild-type worms. (b) Full embryonic development from egg capture in the incubator till hatching, as observed in a sequence of brightfield microscopy images (63× oil immersion objective, NA 1.4) taken from a movie (1 frame per minute) at 45 minute intervals for a N2 wild-type worm strain at 25° C.; the hatching time defines t=0. (c) Illustration of main embryonic development phases—1 cell to bean; bean to 1.5-fold; 1.5-fold to hatching—that are clearly morphologically distinguishable. (d) Duration of development phases, as observed for an array of 20 embryos for a N2 wild-type worm strain at 25° C.; (di) variation of the time duration the embryo spends in an incubator, originating from differences in the exact moment of egg laying and trapping of the embryo; (dii) average duration of development phases, as obtained from the data in (di). (e) Pictures of a full array of 20 embryos taken 600 minutes after trapping in the incubators, Illustrating the blocked development when the embryos are laid by N2 wild-type worms that were exposed in the culture chamber to 2 mM of the anticancer drug 5-fluorouracil (5-FU) in M9 buffer. Bar graphs are expressed as mean+SEM, *** $p \leq 0.001$.
Figure 13:
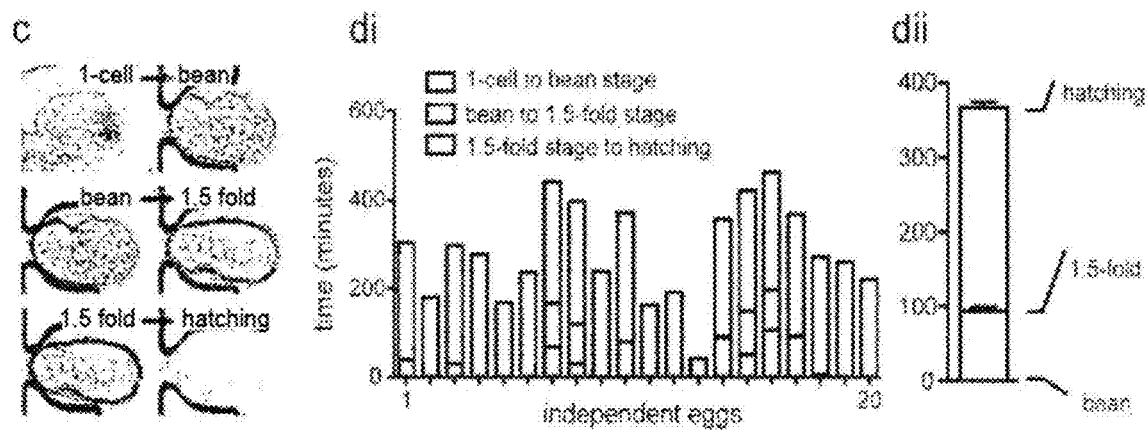
Figure 13:
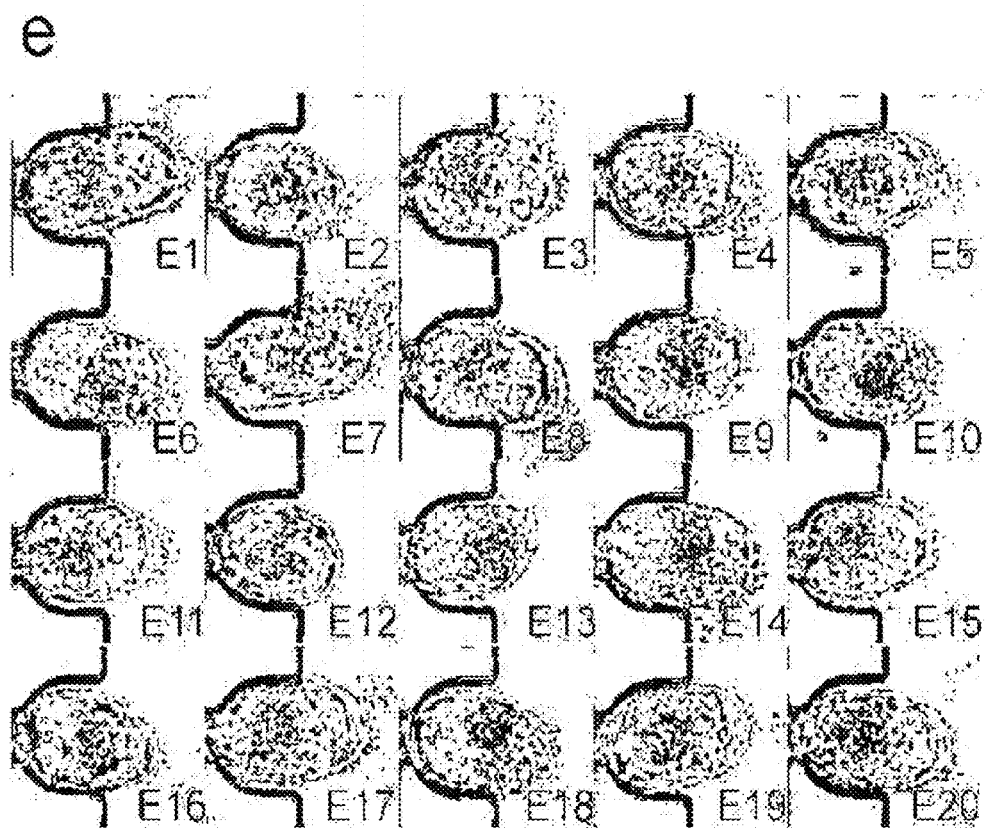

A microscopy environmental control system maintains a constant temperature on the chip (typically 25° C.) over the whole duration of each experiment. An automated xy-positioning stage is used to scan sequentially all positions of interest on the embryo incubator array. Embryos can be monitored at cellular resolution through a 63×, NA 1.4 oil immersion objective, thus allowing accurate observation and analysis of C. elegans embryonic morphogenesis stages (FIG. 13a) over the whole time-span, from egg capture to hatching (FIG. 13b). Two key events with clearly different morphological changes in the embryo shape can be distinguished: (i) the onset of the so-called "bean stage", beginning of morphogenesis (FIG. 13c, top), and (ii) the onset of the "1.5-fold stage", followed by the twitching inception (FIG. 13c, middle). Together with egg hatching (FIG. 13c, bottom), these morphological changes could be detected by software-controlled pattern recognition codes, for the full automation of the image processing. The platform allowed accurate measurement of the duration of these phases for individual N2 wild-type embryos at 25° C. (FIG. 13di). The apparent variability is an indication of variations in the exact moment of egg laying (and subsequent trapping) of each embryo, which represents another interesting phenotype to be studied with this method as well. The average duration of the development phases could be monitored with good accuracy, even from this single array experiment (FIG. 13dii). Moreover, as worms could be cultured and maintained on the same chip for several days, it demonstrates the capability of the device to be employed for studying age-related changes in worm reproduction and progeny development.

Eventually, the possibility of automated on-chip chemical or drug treatment has been validated by exposing the worms to the anticancer drug, 5-fluorouracil (5-FU). This compound induces cell-cycle arrest and apoptosis of germ-line cells in C. elegans. Wild-type worms were isolated in the culture chamber at the L4 larval stage and treated on-chip with 5-FU at a concentration of 2 mM, while being cultured at 25° C. towards the adult stage. Subsequently, embryos were transferred to the incubator array and monitored for 12 h. All embryos prematurely died, proving the efficiency of the drug exposure of the worms in the culture chamber of the chip (FIG. 13e). In the platform, a well-defined and synchronized C. elegans embryo population can be isolated from an on-chip worm culture and studied in a fully automated way at extremely high spatial and temporal resolution. The device allows operation and analysis at the single organism level, thus preserving the identity of each individual embryo, while at the same time providing statistics of the complete population.

It has been demonstrated, through the device of the invention, the capability to accurately analyse the real-time dynamics of different phases of the embryonic development, to monitor live protein expression in developing embryos during the complete embryogenesis, and to perform systematic studies that address outstanding issues in developmental biology. In the future, due to the high versatility of the platform design, its live imaging capability can be readily extended to include other types of microscopies, like differential interference contrast microscopy, for high-contrast brightfield live imaging, and confocal microscopy to achieve extreme spatial resolution. Computer-enhanced image processing can be used to further extend the analytical possibilities of our platform for real-time embryonic screening and phenotyping, or even automated cell lineage and expression profiling in the developing embryos.

As in the platform worms are directly cultured on-chip and embryos analyzed upon spontaneous egg-laying, the whole information related to the natural reproduction process is preserved, maintaining the link between parents and progeny. Therefore, the platform is also suitable for investigating trans-generational properties on the embryos and, with some adaptation of the microfluidic design, even studying the progeny and epigenetic imprints in successive worm generations. Devices for related parasitic nematodes can be readily designed by re-adapting the incubator size, for example to study the effects of antiparasitic drugs. Finally, one could expect that similar microfluidic designs will be used to perform live imaging of a multitude of development events, like gastrulation and tissue morphogenesis during embryogenesis in other species of nematodes or other model organisms.

The invention claimed is:

1. A method for culturing a population of a sample nematode organism by using a system, the system including,
   a microfluidic device having an inlet reservoir configured to hold the sample organism, a culture chamber in fluidic connection with the inlet reservoir, and a valve filter located between the inlet reservoir and the culture chamber, and
   a pressure device operatively connected to the inlet reservoir, the method comprising the steps of:
   providing a population of the sample organism in a fluid culture medium within the inlet reservoir;
   applying a pulse pressure exceeding a threshold pressure to the inlet reservoir so that the fluid culture medium and the sample organism passes from the inlet reservoir to the culture chamber through the valve filter, wherein the valve filter is configured such that application of the threshold pressure allows for size-dependent passage of the sample organism; and
   culturing the sample organism by applying a pressure below the threshold pressure to the inlet reservoir such that only the fluid culture medium passes through the valve filter from the inlet reservoir to the culture chamber, wherein the sample organism is blocked from passing through the valve filter at pressures below the threshold pressure.

2. The method according to claim 1, further comprising the step of:
   analyzing the sample organism by detecting at least one of a specific parameter, a phenotypic characteristic, and a behavioral characteristic of the sample organism.

3. The method of claim 1, wherein the system further comprises other elements that are in fluidic connection with the inlet reservoir and the culture chamber, and the below-threshold pressure causes the fluid culture medium to pass through the valve filter from the inlet reservoir to the culture chamber and to the other elements.

4. The method of claim 1 further including steps for screening active compounds, the steps for screening active compounds comprising:
   providing an active compound to be screened in the inlet reservoir;
   monitoring an effect of the active compound on the sample organism within the culture chamber.

5. The method according to claim 1, wherein the culture chamber includes a plurality of adjacent culture chambers, each one of the plurality of adjacent culture chambers connected to the inlet reservoir.

6. The method according to claim 1, wherein the system further includes a plurality of adjacent channels forming consecutive culture chambers, each one of the plurality of channels connected with the inlet reservoir via a proximal chamber.

* * * * *